(12) United States Patent
Phillips et al.

(10) Patent No.: US 9,649,502 B2
(45) Date of Patent: May 16, 2017

(54) DEVICES AND METHODS OF LOW FREQUENCY MAGNETIC STIMULATION THERAPY

(71) Applicant: NeoSync, Inc., Newport Beach, CA (US)

(72) Inventors: James William Phillips, Fountain Valley, CA (US); Yi Jin, Irvine, CA (US)

(73) Assignee: NEOSYNC, INC., Newton, MA (US)

( * ) Notice: Subject to any disclaimer, the term of this patent is extended or adjusted under 35 U.S.C. 154(b) by 157 days.

(21) Appl. No.: 13/675,466

(22) Filed: Nov. 13, 2012

(65) Prior Publication Data

US 2013/0137918 A1 May 30, 2013

Related U.S. Application Data

(60) Provisional application No. 61/559,490, filed on Nov. 14, 2011.

(51) Int. Cl.
*A61N 2/02* (2006.01)
*A61N 2/00* (2006.01)
*A61N 2/06* (2006.01)

(52) U.S. Cl.
CPC ............... *A61N 2/02* (2013.01); *A61N 2/006* (2013.01); *A61N 2/06* (2013.01)

(58) Field of Classification Search
CPC ... A61N 2/02; A61N 2/06; A61N 2/12; A61N 2/006; A61N 1/40; A61N 1/37229;
(Continued)

(56) References Cited

U.S. PATENT DOCUMENTS

| 3,821,949 A | 7/1974 | Hartzell et al. |
|---|---|---|
| 4,727,857 A | 3/1988 | Horl |

(Continued)

FOREIGN PATENT DOCUMENTS

| DE | 29821635 U1 | 8/1998 |
|---|---|---|
| DE | 29821635 U1 | 7/1999 |

(Continued)

OTHER PUBLICATIONS

PCT/US08/77569 Preliminary Report on Patentability dated Mar. 30, 2010.

(Continued)

*Primary Examiner* — Navin Natnithithadha
*Assistant Examiner* — Sunita Reddy
(74) *Attorney, Agent, or Firm* — Wilson Sonsini Goodrich & Rosati

(57) ABSTRACT

Described herein, in certain embodiments, are devices and methods for modulating the electrical activity of a brain in a targeted manner using a weak magnetic field, generally field with a strength of less than about 100 Gauss. The magnetic field is varied over time in a periodic manner, generally with a frequency tuned to specifically affect one of the intrinsic frequencies of the brain, optionally the alpha frequency. The "Low Field Magnetic Stimulation" devices and methods described herein modulate the electrical activity of a brain without requiring medication. Methods and devices described herein gently "tune" the brain and affect mood, focus, and cognition of human subjects.

20 Claims, 17 Drawing Sheets

(58) Field of Classification Search
CPC ......... A61B 5/0476; A61B 5/055; A61B 5/06; G01R 33/3415
USPC ............. 600/9–15, 417; 128/897–899; 607/2
See application file for complete search history.

(56) References Cited

U.S. PATENT DOCUMENTS

| | | | |
|---|---|---|---|
| 5,036,858 A | 8/1991 | Carter et al. | |
| 5,092,835 A | 3/1992 | Schurig et al. | |
| 5,409,445 A | 4/1995 | Rubins | |
| 5,453,072 A | 9/1995 | Anninos et al. | |
| 5,496,258 A | 3/1996 | Anninos et al. | |
| 5,632,720 A | 5/1997 | Kleitz | |
| 5,667,469 A | 9/1997 | Zhang et al. | |
| 5,691,324 A * | 11/1997 | Sandyk | 514/159 |
| 5,697,883 A | 12/1997 | Anninos et al. | |
| 5,707,334 A | 1/1998 | Young | |
| 5,769,778 A | 6/1998 | Abrams et al. | |
| 5,788,624 A | 8/1998 | Lu et al. | |
| 5,935,054 A | 8/1999 | Loos | |
| 5,954,629 A | 9/1999 | Yanagidaira et al. | |
| 6,001,055 A | 12/1999 | Souder | |
| 6,083,252 A | 7/2000 | King et al. | |
| 6,157,278 A | 12/2000 | Katznelson et al. | |
| 6,231,497 B1 | 5/2001 | Souder | |
| 6,234,953 B1 | 5/2001 | Thomas et al. | |
| 6,238,333 B1 | 5/2001 | Loos | |
| 6,266,556 B1 | 7/2001 | Ives et al. | |
| 6,290,638 B1 | 9/2001 | Canedo et al. | |
| 6,402,678 B1 | 6/2002 | Fischell et al. | |
| 6,463,328 B1 | 10/2002 | John | |
| 6,488,617 B1 | 12/2002 | Katz | |
| 6,537,197 B1 | 3/2003 | Ruohonen et al. | |
| 6,648,812 B2 | 11/2003 | Ardizzone | |
| 6,663,557 B2 | 12/2003 | Werny | |
| 6,679,825 B2 | 1/2004 | Alicea | |
| 6,978,179 B1 | 12/2005 | Flagg et al. | |
| 7,033,312 B2 | 4/2006 | Rohan et al. | |
| 7,102,144 B2 | 9/2006 | Matsuda et al. | |
| 7,258,659 B2 | 8/2007 | Anninou et al. | |
| 7,282,021 B2 | 10/2007 | Rohan et al. | |
| 7,297,100 B2 | 11/2007 | Thomas et al. | |
| 8,465,408 B2 | 6/2013 | Phillips et al. | |
| 8,475,354 B2 | 7/2013 | Phillips et al. | |
| 8,480,554 B2 | 7/2013 | Phillips et al. | |
| 8,585,568 B2 | 11/2013 | Phillips et al. | |
| 8,870,737 B2 | 10/2014 | Phillips et al. | |
| 8,888,672 B2 | 11/2014 | Phillips et al. | |
| 8,888,673 B2 | 11/2014 | Phillips et al. | |
| 8,926,490 B2 | 1/2015 | Phillips et al. | |
| 8,961,386 B2 | 2/2015 | Phillips et al. | |
| 9,015,057 B2 | 4/2015 | Phillips et al. | |
| 9,446,259 B2 | 9/2016 | Phillips et al. | |
| 2002/0007128 A1 | 1/2002 | Ives et al. | |
| 2003/0093028 A1 | 5/2003 | Spiegel | |
| 2004/0138578 A1 | 7/2004 | Pineda et al. | |
| 2004/0143296 A1 | 7/2004 | Wang | |
| 2004/0210102 A1* | 10/2004 | van Mullekom | 600/9 |
| 2005/0043774 A1 | 2/2005 | Devlin et al. | |
| 2005/0070778 A1 | 3/2005 | Lackey et al. | |
| 2005/0107654 A1 | 5/2005 | Riehl | |
| 2005/0107655 A1 | 5/2005 | Holzner | |
| 2005/0118286 A1 | 6/2005 | Suffin et al. | |
| 2005/0124847 A1 | 6/2005 | Ardizzone et al. | |
| 2005/0124848 A1 | 6/2005 | Holzner | |
| 2005/0154426 A1 | 7/2005 | Boveja et al. | |
| 2005/0182287 A1 | 8/2005 | Becker | |
| 2005/0187423 A1 | 8/2005 | Ardizzone et al. | |
| 2005/0228209 A1 | 10/2005 | Schneider | |
| 2005/0256539 A1 | 11/2005 | George et al. | |
| 2006/0015153 A1 | 1/2006 | Gliner et al. | |
| 2006/0058572 A1 | 3/2006 | Anninou et al. | |
| 2006/0094924 A1 | 5/2006 | Riehl | |
| 2006/0149119 A1 | 7/2006 | Wang | |
| 2006/0161039 A1 | 7/2006 | Juliana et al. | |
| 2006/0189866 A1 | 8/2006 | Thomas et al. | |
| 2006/0212090 A1 | 9/2006 | Lozano et al. | |
| 2006/0217781 A1 | 9/2006 | John | |
| 2006/0258950 A1 | 11/2006 | Hargrove et al. | |
| 2007/0004957 A1 | 1/2007 | Hilburg | |
| 2007/0100389 A1 | 5/2007 | Jaax et al. | |
| 2007/0106170 A1 | 5/2007 | Dunseath, Jr. et al. | |
| 2007/0142874 A1 | 6/2007 | John | |
| 2007/0179558 A1 | 8/2007 | Gliner et al. | |
| 2007/0191727 A1 | 8/2007 | Fadem | |
| 2007/0203390 A1 | 8/2007 | Rohan et al. | |
| 2007/0208209 A1 | 9/2007 | Holcomb | |
| 2007/0282156 A1 | 12/2007 | Konings | |
| 2008/0009772 A1 | 1/2008 | Tyler et al. | |
| 2008/0046013 A1 | 2/2008 | Lozano | |
| 2008/0081941 A1 | 4/2008 | Tononi | |
| 2008/0125669 A1 | 5/2008 | Suffin et al. | |
| 2009/0082690 A1 | 3/2009 | Phillips et al. | |
| 2009/0083071 A1 | 3/2009 | Phillips | |
| 2009/0198144 A1 | 8/2009 | Phillips | |
| 2009/0204015 A1 | 8/2009 | Phillips | |
| 2011/0034822 A1 | 2/2011 | Phillips et al. | |
| 2011/0112427 A1 | 5/2011 | Phillips et al. | |
| 2011/0118536 A1 | 5/2011 | Phillips et al. | |
| 2011/0137104 A1 | 6/2011 | Phillips et al. | |
| 2013/0144106 A1 | 6/2013 | Phillips et al. | |
| 2013/0144107 A1 | 6/2013 | Phillips et al. | |
| 2013/0144108 A1 | 6/2013 | Phillips et al. | |
| 2013/0150650 A1 | 6/2013 | Phillips et al. | |
| 2013/0150651 A1 | 6/2013 | Phillips et al. | |
| 2014/0121446 A1 | 5/2014 | Phillips et al. | |

FOREIGN PATENT DOCUMENTS

| | | |
|---|---|---|
| WO | WO-96-15829 A2 | 5/1996 |
| WO | WO-96-29114 A1 | 9/1996 |
| WO | WO-03-058518 A2 | 7/2003 |
| WO | WO-2007-067148 A1 | 6/2007 |
| WO | WO-2008-074707 | 6/2008 |
| WO | WO-2009-042718 | 4/2009 |
| WO | WO-2009-042720 | 4/2009 |
| WO | WO-2009-042721 | 4/2009 |
| WO | WO-2009-042722 | 4/2009 |
| WO | WO-2011-017466 | 2/2011 |
| WO | WO-2011-059986 | 5/2011 |

OTHER PUBLICATIONS

PCT/US08/77571 Preliminary Report on Patentability dated Mar. 30, 2010.
PCT/US08/77571 Written Opinion dated Nov. 21, 2008.
PCT/US08/77573 Preliminary Report on Patentability dated Mar. 30, 2010.
PCT/US08/77573 Written Opinion dated Nov. 24, 2008.
PCT/US08/77575 Preliminary Report on Patentability dated Mar. 30, 2010.
PCT/US10/056075 Preliminary Report on Patentability dated May 24, 2012.
PCT/US10/44465 Preliminary Report on Patentability dated Feb. 7, 2012.
U.S. Appl. No. 12/944,549 Office Action dated Mar. 25, 2014.
U.S. Appl. No. 12/944,549 Office Action dated Sep. 13, 2013.
U.S. Appl. No. 12/237,295 Office Action dated Oct. 21, 2013.
U.S. Appl. No. 12/237,304 Office Action dated Sep. 25, 2013.
U.S. Appl. No. 12/944,591 Office Action dated Apr. 7, 2014.
U.S. Appl. No. 12/944,591 Office Action dated Sep. 23, 2013.
U.S. Appl. No. 13/681,964 Office Action dated Jan. 22, 2014.
U.S. Appl. No. 13/682,057 Office Action dated Jan. 22, 2014.
U.S. Appl. No. 13/682,098 Office Action dated Jan. 24, 2014.
U.S. Appl. No. 13/682,147 Office Action dated Apr. 25, 2013.
U.S. Appl. No. 13/682,147 Office Action dated Dec. 20, 2013.
U.S. Appl. No. 13/682,181 Office Action dated Feb. 12, 2014.
Angelakis et al., "EEG Neurofeedback: A brief overview and an example of peak alpha frequency training for cognitive enhancement in the elderly," Clin. Neuropsychol., 21(1):110-29 (2007).

(56) References Cited

OTHER PUBLICATIONS

Anninos et al., "MEG evaluation of Parkinson's diseased patients after external magnetic stimulation," Acta neurol. Belg. 107:5-10 (2007).
Anninos et al., "Nonlinear Analysis of Brain Activity in Magnetic Influenced Parkinson Patients," Brain Topography 13(2):135-144 (2000).
Applied Signal Processing. (2004) 20 pgs., http://users.abo.fi/htoivone/courses/sbappl/asp_chapter1.pdf.
Arns et al., "Potential differential effects of 9Hz rTMS and 10 Hz rTMS in the treatment of depression," Letter to the Editor, Brain Stimulation (2010), 3, 124-126.
Blum, "Computer-based electroencephalography: technical basics, basis for new applications, and potential pitfalls," Electroencephalography and Clinical Neurophysiology 106, pp. 118-126 (1998).
Discovery Science: Transcranial Magnetic Stimulation Treatment for Addiction, Autism, Depression (Dr. Yi Jin) from PopSci's *Future of Pleasure* originally broadcast Oct. 26, 2009 [online][retrieved on Dec. 16, 2011] Retrieved from the Internet: http://www.youtube.com/watch?v=E3tPuB31CYc.
EP08833077 Supplementary Search Report and Written Opinion dated Dec. 21, 2010.
First Annual Brain and Behavior Symposium: The Future of the Brain (Dr. Yi Jin) (Jun. 8, 2007) [online][retrieved on Dec. 16, 2011] Retrieved from the Internet: http://neurosciencecenter.brooksideinstitute.com/2007_symposium_03Speaker. asp.
Gasquet et al., "Pharmacological treatment and other predictors of treatment outcomes in previously untreated patients with schizophrenia; results from the European Schizophrenia Outpatient Health Outcomes (SOHO) study," Int. Clin. Psychopharmacol. 20:199-205 (2005).
Gaussian Peak Fit VI., LabVIEW 2009 Help. National Instruments. 4 pgs., Jun. 2009.
Hamidi et al., "Repetitive transcranial magnetic stimulation affects behavior by biasing endogenous cortical oscillations," Frontiers in Integrative Neuroscience 3(14):1-12 (2009).
Jin, Y. et al., "Alpha EEG predicts visual reaction time," Int. J. Neurosci. 116:1035-1044 (2006).
Jin, Y. et al., "Therapeutic effects of individualized alpha frequency transcranial magnetic stimulation (alpha TMS) on the negative symptoms of schizophrenia," Schizophr. Bull. 32(3):556-561 (Jul. 2006;Epub Oct. 27, 2005).
Klimesch et al., "EEG alpha oscillations: The inhibition-timing hypothesis," Brain Research Reviews 53:63-88 (2003).
Klimesch et al., "Enhancing cognitive performance with repetitive transcranial magnetic stimulation at human individual alpha frequency," Eur. J. Neuroscience 17:1129-1133 (2003).
MERT: Magno-EEG Resonant Therapy (Aug. 29, 2007)[online][retrieved on Dec. 19, 2011] Retrieved from the Internet: http://web.archive.org/web/20080514214345/http://neurosciencecenter.brooksideinstitute.com/mert.asp; http://web.archive.org/web/20080514161113/http://neurosciencecenter.brooksideinstitute.com/mert_disorder.asp; and http://web.archive.org/web/20080509095813/http://neurosciencecenter.brooksideinstitute.com/mertfaq.asp.
Myung, "Tutorial on Maximum Likelihood Estimation," Journal of Mathematical Psychology, 47, pp. 90-100 (2003).
O'Haver, "Curve Fitting C: Non-Linear Iterative Curve Fitting," Jun. 6, 2009. http://web.archive.org/web/20090606121639/http://terpconnect.umd.edu/~toh/spectrum/CurveFittingC.html.
PCT/US08/77569 Search Report dated Jan. 26, 2009.
PCT/US08/77569 Written Opinion dated Jan. 26, 2009.
PCT/US08/77571 Search Report dated Nov. 21, 2008.
PCT/US08/77573 Search Report dated Nov. 24, 2008.
PCT/US08/77575 Search Report dated Dec. 9, 2008.
PCT/US10/056075 Search Report and Written Opinion mailed Mar. 14, 2011.
PCT/US10/44465 Search Report and Written Opinion mailed Sep. 29, 2010.
Real-Time Filtering in BioExplorer. Jan. 25, 2007. http://web.archive.org/web/20070125020332/http://www.brain-trainer.com/Filtering.pdf.
Sauseng et al., "Spontaneous locally restricted EEG alpha activity determines cortical excitability in the motor cortex," Neuropsychologia 47:284-288 (2009).
Triggs et al., "Effects of Left Frontal Transcranial Magnetic Stimulation on Depressed Mood, Cognition, and Corticomotor Threshold," Society of Biological Psychiatry 1999.
U.S. Appl. No. 12/237,295 Office Action dated Dec. 6, 2011.
U.S. Appl. No. 12/237,295 Office Action dated May 9, 2011.
U.S. Appl. No. 12/237,304 Office Action dated Jul. 3, 2012.
U.S. Appl. No. 12/237,319 Office Action Oct. 14, 2011.
U.S. Appl. No. 12/237,319 Office Action Jul. 19, 2012.
U.S. Appl. No. 12/237,328 Office Action dated Oct. 12, 2011.
U.S. Appl. No. 12/237,328 Office Action dated Jul. 19, 2012.
U.S. Appl. No. 12/850,547 Office Action dated Oct. 13, 2011.
U.S. Appl. No. 12/850,547 Office Action dated Jul. 19, 2012.
U.S. Appl. No. 12/942,922 Office Action dated Nov. 19, 2012.
What is TMS? (Jun. 8, 2011) [online][retrieved on Dec. 19, 2011] Retrieved from the Internet: http://web.archive.org/web/20101014023718/http://braintreatmentcenter.com/tms.html; and http://www.braintreatmentcenter.com/addiction.
U.S. Appl. No. 12/237,295 Office Action dated May 23, 2014.
U.S. Appl. No. 13/682,057 Office Action dated Jul. 11, 2014.
U.S. Appl. No. 13/682,057 Office Action dated Nov. 5, 2014.
U.S. Appl. No. 13/682,098 Office Action dated Jun. 30, 2014.
U.S. Appl. No. 13/682,181 Office Action dated Jun. 27, 2014.
U.S. Appl. No. 13/682,181 Notice of Allowance dated Oct. 10, 2014.
U.S. Appl. No. 13/675,466 Office Action dated Aug. 1, 2014.
U.S. Appl. No. 13/893,171 Office Action dated Aug. 29, 2014.
U.S. Appl. No. 12/237,295 Notice of Allowance mailed Dec. 5, 2014.
U.S. Appl. No. 12/237,304 Office Action dated Feb. 12, 2015.
U.S. Appl. No. 13/682,098 Office Action dated Feb. 11, 2015.
U.S. Appl. No. 13/893,171 Office Action dated Jan. 2, 2015.
U.S. Appl. No. 14/051,378 Office Action dated Jan. 5, 2015.
Arns et al., Letter to the editor. Potential differential effects of 9 Hz rTMS and 10 Hz rTMS in the treatment of depression. Brain Stimulation, 3:124-126 (2010).
Leuchter, et al., The relationship between brain oscillatory activity and therapeutic effectiveness of transcranial magnetic stimulation in the treatment of major depressive disorder. Frontiers in Human Neuroscience. vol. 7, Article 37, pp. 1-12. Feb. 26, 2013.
U.S. Appl. No. 13/682,057 Office Action dated Mar. 12, 2015.
U.S. Appl. No. 12/237,304 Office Action mailed Oct. 8, 2015.
U.S. Appl. No. 13/682,057 Office Action mailed Jun. 30, 2015.
U.S. Appl. No. 13/682,098 Office Action mailed Aug. 14, 2015.
U.S. Appl. No. 14/051,378 Office Action mailed Jul. 30, 2015.
European Patent Application No. 08833077.4 Communication dated May 23, 2016.
European Patent Application No. 10830602.8 Communication dated Jun. 30, 2016.

\* cited by examiner

DEVICES AND METHODS OF LOW FREQUENCY MAGNETIC STIMULATION THERAPY

BACKGROUND OF THE INVENTION

A neurological disorder generates serious problems for the affected subjects, their families, and society. Currently, psychiatrists and neurophysiologists treat these disorders with a variety of medications, many of which have significant negative side effects.

Repetitive Transcranial Magnetic Stimulation (rTMS) uses an electromagnet placed on the scalp that generates a series of magnetic field pulses roughly the strength of an MRI scan. Some studies have shown that rTMS can reduce the negative symptoms of schizophrenia and depression under certain circumstances. Both rTMS and MRI generate a strong magnetic field, generally greater than about 6,000 Gauss which has a strong and broad-based effect on the brain.

SUMMARY OF THE INVENTION

Described herein, in certain embodiments, are devices and methods for modulating the electrical activity of a brain in a targeted manner using a weak magnetic field, generally field with a strength of less than about 100 Gauss. The magnetic field is varied over time in a periodic manner, generally with a frequency tuned to specifically affect one of the intrinsic frequencies of the brain, optionally the alpha frequency. The "Low Field Magnetic Stimulation" devices and methods described herein modulate the electrical activity of a brain without requiring medication. Methods and devices described herein gently "tune" the brain and affect mood, focus, and cognition of human subjects.

In one aspect described herein is a device for use in treating a subject, comprising: a Low Field Magnetic Stimulation (LFMS) device; wherein the LFMS device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller capable of adjusting the frequency or pulsing of the device.

In one aspect described herein is a device for use in treating a subject, comprising: a Magnetic Resonance Imaging (MRI) device; wherein the MRI device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller capable of adjusting the frequency or pulsing of the device.

In one aspect described herein is a Low Field Magnetic Stimulation device comprising: a user interface; a waveform generator in communication with the user interface, wherein the waveform generator is capable of creating an electrical waveform; and at least one coil capable of converting the electrical waveform into a magnetic field, wherein the user interface can be used to adjust the waveform to create a magnetic field influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein at least one of (a) the strength of the magnetic field is less than about 100 Gauss, (b) the magnetic field is substantially uniform, (c) the magnetic field targets substantially the whole brain, and (d) the waveform has a frequency of less than about 100 Hz. In some embodiments, the device further comprises an amplifier capable of modifying the waveform.

In one aspect described herein is a device for treating a subject comprising: a Low Field Magnetic Stimulation device capable of generating a magnetic field for one or more of the following: influencing an intrinsic frequency of a specified EEG band of the subject toward a target intrinsic frequency of the specified EEG band, for influencing a Q-factor of an intrinsic frequency within a specified EEG band of the subject toward a target Q-factor, influencing a coherence of intrinsic frequencies among multiple sites in a brain of the subject within a specified EEG band toward a target coherence value; influencing an EEG phase between two sites in the brain of a subject of a specified EEG frequency toward a target EEG phase of the specified EEG frequency; and the device is capable of applying said magnetic field to the head of the subject.

In one aspect described herein is a device for treating a subject comprising: a Low Field Magnetic Stimulation device capable of adjusting an intrinsic frequency of the subject by applying a magnetic field to the head of the subject, wherein the magnetic field comprises at least one of (a) a single target frequency; (b) a plurality of frequencies within a specified EEG band; and (c) an intrinsic frequency of a brain of the subject within a specified EEG band.

In one aspect described herein is a device for treating a subject comprising: a Magnetic Resonance Imaging (MRI) device capable of generating a magnetic field for one or more of the following: influencing an intrinsic frequency of a specified EEG band of the subject toward a target intrinsic frequency of the specified EEG band, for influencing a Q-factor of an intrinsic frequency within a specified EEG band of the subject toward a target Q-factor, influencing a coherence of intrinsic frequencies among multiple sites in a brain of the subject within a specified EEG band toward a target coherence value; influencing an EEG phase between two sites in the brain of a subject of a specified EEG frequency toward a target EEG phase of the specified EEG frequency; and the device is capable of applying said magnetic field to the head of the subject.

In one aspect described herein is a device for treating a subject comprising: a Magnetic Resonance Imaging (MRI) device capable of adjusting an intrinsic frequency of the subject by applying a magnetic field to the head of the subject, wherein the magnetic field comprises at least one of (a) a single target frequency; (b) a plurality of frequencies within a specified EEG band; and (c) an intrinsic frequency of a brain of the subject within a specified EEG band.

In one aspect described herein is a method for treating a subject comprising influencing the brain of the subject with a magnetic field having a specified frequency, wherein the magnetic field has a strength of less than about 100 Gauss, wherein the specified frequency is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the brain is influenced with a Low Field Magnetic Stimulator (LFMS), a Magnetic Resonance Imager (MRI), a Transcranial Magnetic Stimulator (TMS), a Neuro-EEG Synchronization Therapy device, a picoTesla™ device, or any combination thereof.

In one aspect described herein is a method for treating a subject comprising: adjusting the output of a Low Field Magnetic Stimulation (LFMS) device to generate a magnetic field for one or more of the following: influencing an intrinsic frequency of a specified EEG band of the subject toward a target intrinsic frequency of the specified EEG band, for influencing a Q-factor of an intrinsic frequency within a specified EEG band of the subject toward a target Q-factor, influencing a coherence of intrinsic frequencies among multiple sites in a brain of the subject within a specified EEG band toward a target coherence value; influencing an EEG phase between two sites in the brain of a subject of a specified EEG frequency toward a target EEG phase of the specified EEG frequency; and applying said magnetic field to a head of the subject. The LFMS in some embodiments is close to the head of the subject. In some embodiments the LFMS, or a portion thereof, is touching the subject. In some embodiments the LFMS, or a portion thereof, is touching the head of the subject.

In one aspect described herein is a method for treating a subject comprising: adjusting an intrinsic frequency of the subject by applying a magnetic field generated from a Low Field Magnetic Stimulation device to the head of the subject, wherein the magnetic field comprises at least one of (a) a single target frequency; (b) a plurality of frequencies within a specified EEG band; and (c) an intrinsic frequency of a brain of the subject within a specified EEG band.

In one aspect described herein is a method for treating a subject comprising pulsing an MRI with a wave train having a frequency capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof. In some embodiments, the MRI does not detect magnetic fields. In some embodiments, the wave train is applied to the head of the subject.

In one aspect described herein is a method of altering an intrinsic frequency of a brain of a subject within a specified EEG band, comprising: determining the intrinsic frequency of the subject within the specified EEG band; comparing the intrinsic frequency from step (a) to an average intrinsic frequency of a control group; if the intrinsic frequency from step (a) is higher than the average intrinsic frequency of the control group, shifting down the intrinsic frequency of the subject by applying a specific magnetic field generated from a LFMS device to a head of the subject, wherein said specific magnetic field has a frequency lower than the intrinsic frequency of the subject; and if the intrinsic frequency from step (a) is lower than the average intrinsic frequency of the control group, shifting up the intrinsic frequency of the subject by applying a specific magnetic field generated from a LFMS device to a head of the subject, wherein said specific magnetic field has a frequency higher than the intrinsic frequency of the subject. The LFMS in some embodiments is close to the head of the subject. In some embodiments the LFMS, or a portion thereof, is touching the subject. In some embodiments the LFMS, or a portion thereof, is touching the head of the subject.

In one aspect described herein is a method of modulating the electrical activity of a brain in a subject in need thereof, comprising: determining the Q-factor of the intrinsic frequency within the specified EEG band of the subject; comparing the Q-factor of the intrinsic frequency from step (a) to an average Q-factor of the intrinsic frequency of a control group; if the Q-factor of the intrinsic frequency from step (a) is higher than the average Q-factor of the intrinsic frequency of the control group, tuning down the Q-factor of the intrinsic frequency of the subject by applying a magnetic field with a plurality of frequencies or with a single target frequency generated from a LFMS device to a head of the subject; and if the Q-factor of the intrinsic frequency from step (a) is lower than the average Q-factor of the intrinsic frequency of the control group, tuning up the Q-factor of the intrinsic frequency of the subject by applying a magnetic field with a target frequency generated from a LFMS device to a head of the subject. The LFMS in some embodiments is close to the head of the subject. In some embodiments the LFMS, or a portion thereof, is touching the subject. In some embodiments the LFMS, or a portion thereof, is touching the head of the subject.

In one aspect described herein is a method for influencing a coherence of intrinsic frequencies among multiple sites in a brain of the subject within a specified EEG band toward a target coherence value comprising: determining the coherence value of the intrinsic frequencies among multiple locations throughout a scalp of the subject; comparing the coherence value from step (a) to an average coherence value of a control group; if the coherence value from step (a) is higher than the average coherence value of the control group, lowering the coherence value of the subject by applying at least two asynchronous magnetic fields generated from a LFMS device to a head of the subject; and if the coherence value from step (a) is lower than the average coherence value of the control group, raising the coherence value of the subject by applying at least one synchronized magnetic field generated from a LFMS device to a head of the subject. The LFMS in some embodiments is close to the head of the subject. In some embodiments the LFMS, or a portion thereof, is touching the subject. In some embodiments the LFMS, or a portion thereof, is touching the head of the subject.

In one aspect described herein is a method for influencing an EEG phase of a specified EEG frequency between multiple locations of a brain of a subject, comprising: determining the EEG phase the between at least two locations measured on the head of the subject; comparing the EEG phase from step (a) to an average EEG phase of a control group; and applying a magnetic field generated from a LFMS device to a head of the subject wherein applying the magnetic field influences the determined EEG phase toward the average EEG phase of a control group. The LFMS in some embodiments is close to the head of the subject. In some embodiments the LFMS, or a portion thereof, is touching the subject. In some embodiments the LFMS, or a portion thereof, is touching the head of the subject.

In some embodiments, the specified EEG band is an alpha wave, a beta wave, a gamma wave, a mu wave, a delta wave, a theta wave, or any combination thereof.

In some embodiments, the target intrinsic frequency is any one or more of: the subject's intrinsic frequency; the intrinsic frequency of an individual having a disorder, a disease, a deficient mental characteristic, or any combination thereof; the intrinsic frequency of an individual not having the disorder, the disease, the deficient mental characteristic, or any combination thereof; the average intrinsic frequency of a population of individuals having a disorder, a disease, a deficient mental characteristic, or any combination thereof; and the average intrinsic frequency of a population of individuals not having the disorder, the disease, the deficient mental characteristic, or any combination thereof.

In some embodiments, the target Q-factor is any one or more of: the subject's intrinsic Q-factor; the intrinsic Q-factor of an individual having a disorder, a disease, a deficient mental characteristic, or any combination thereof; the intrinsic Q-factor of an individual not having the disorder, the disease, the deficient mental characteristic, or any combination thereof the average intrinsic Q-factor of a population of individuals having a disorder, a disease, a deficient mental characteristic, or any combination thereof; and the average intrinsic Q-factor of a population of individuals not having the disorder, the disease, the deficient mental characteristic, or any combination thereof.

In some embodiments, the target coherence is any one or more of: the subject's intrinsic coherence; the intrinsic coherence of an individual having a disorder, a disease, a deficient mental characteristic, or any combination thereof; the intrinsic coherence of an individual not having the disorder, the disease, the deficient mental characteristic, or any combination thereof; the average intrinsic coherence of a population of individuals having a disorder, a disease, a deficient mental characteristic, or any combination thereof; and the average intrinsic coherence of a population of individuals not having the disorder, the disease, the deficient mental characteristic, or any combination thereof.

In some embodiments, the target EEG phase is any one or more of: the subject's intrinsic EEG phase; the intrinsic EEG phase of an individual having a disorder, a disease, a deficient mental characteristic, or any combination thereof; the intrinsic EEG phase of an individual not having the disorder, the disease, the deficient mental characteristic, or any combination thereof; the average intrinsic EEG phase of a population of individuals having a disorder, a disease, a deficient mental characteristic, or any combination thereof; and the average intrinsic EEG phase of a population of individuals not having the disorder, the disease, the deficient mental characteristic, or any combination thereof.

In some embodiments, at least one brain parameter is measured in the subject.

In some embodiments, the brain parameter comprises an intrinsic frequency, an intrinsic Q-factor, an intrinsic coherence, an intrinsic EEG phase, and any combination thereof.

In some embodiments, the method for measuring the brain parameter comprises: placing a first electrode on the back of the head of the subject; placing a second electrode on the front of the head of the subject; placing a ground electrode on the subject; connecting the electrodes to a device; and measuring the brain parameter with the electrodes.

In some embodiments, the first electrode is a sensing electrode and the second electrode is a reference electrode. In some embodiments, the first electrode is placed above the occipital region and/or approximately 1 inch above the inion protrusion. In some embodiments, the second electrode is placed approximately one inch above the bridge between the eyebrows and/or directly in front of the pre-frontal cortex.

In some embodiments, the patient's brain parameter is determined by the device described herein. In some embodiments, the patient's brain parameter is entered into the device described herein. In some embodiments, the brain parameter is entered through the user interface, is entered from external memory device, or is entered from a network connection.

In some embodiments, the subject is treated for about 1 minute to about 30 minutes. In some embodiments, the subject is treated for about 30 minutes to about 40 minutes. In some embodiments, the treatment is repeated after an interval of about 6 hours to about 14 days.

In some embodiments, the magnetic field is generated using at least one coil. In some embodiments, the coil is configured to encircle the head of the subject. In some embodiments, a plurality of coils are configured around the head of the subject. In some embodiments, the coil is configured to be positioned over a region of interest on the head of the subject. In some embodiments, the coil is configured to cover the prefrontal cortex of the subject.

In some embodiments, the device emits, but does not detect magnetic fields.

In some embodiments, the device further comprises a module capable of determining at least one brain parameter of the subject.

In some embodiments, the brain of the subject is stimulated to a level below the threshold for depolarization of the neurons in the brain of the subject.

In some embodiments, the magnetic field is substantially uniform. In some embodiments, the magnetic field strength varies substantially linearly. In some embodiments, the magnetic field has no gradient greater than about 5 Gauss/cm. In some embodiments, the magnetic field is unidirectional. In some embodiments, the magnetic field is applied to a diffuse area of the brain of the subject.

In some embodiments, the magnetic field varies according to a waveform. In some embodiments, the waveform is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec. In some embodiments, the waveform has a frequency between about 8 Hz and about 13 Hz.

In some embodiments, the strength of the magnetic field is less than about 100 Gauss. In some embodiments, the strength of the magnetic field is less than about 500 milligauss.

In some embodiments, the subject is treated for major depression, depression, bipolar disorder, schizophrenia, anxiety disorder, obsessive-compulsive disorder, attention deficit hyperactivity disorder (ADHD), autism, autism spectrum disorders, sleep disorder, Parkinson's Disease, drug addiction, substance abuse, seizure, traumatic brain injury, Alzheimer's Disease, eating disorder, tinnitus, fibromyalgia, coma, post-traumatic stress disorder (PTSD), and any combination thereof.

In some embodiments, the treatment comprises improving cognitive function, executive function, academic performance, sports performance, peripheral visual response, attention span, immediate reaction time (IRT), movement time (MT), simple perceptual reaction time (SPR), conflict perceptual reaction time (CPR), or any combination thereof.

In some embodiments, the treatment comprises improving at least one of: an indication in the subject; a disorder in the subject; a symptom in the subject; a dysfunction in the subject; a characteristic in the subject; and any combination thereof.

In some embodiments, the indication is selected from the group consisting of replacement for meditation, quick nap, stress release, attention span, comprehension, memory, lowered blood pressure, increased libido, sports performance, academic performance, and any combination thereof.

In some embodiments, the disorder is selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof.

In some embodiments, the characteristic is selected from the group consisting of peripheral visual response, attention span, immediate reaction time (IRT), movement time (MT), simple perceptual reaction time (SPR), conflict perceptual reaction time (CPR), and any combination thereof.

In some embodiments, the treatment increases blood flow in the cortex of the subject.

In some embodiments, the treatment improves at least one of neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, epilepsy, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

Provided herein is a Low Field Magnetic Stimulation device comprising: a user interface; a waveform generator in communication with the user interface, wherein the waveform generator creates an electrical waveform; and at least one coil that converts the electrical waveform into a magnetic field, wherein the user interface comprises a controller configured to allow adjustment of the waveform to create the magnetic field that influences (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, wherein at least one of (a) a strength of the magnetic field is less than about 100 Gauss, (b) the magnetic field is substantially uniform, (c) the magnetic field is configured to target substantially the whole brain, and (d) the waveform has a frequency of less than about 100 Hz, and wherein controller allows adjustment of a frequency of the magnetic field, adjustment of a frequency of the waveform, or can be used to pulse of the magnetic field.

In some embodiments, the magnetic field is generated by a coil configured to encircle the head of the subject, wherein the magnetic field is generated by a plurality of coils around the head of the subject, or wherein the magnetic field is generated by a coil that can be positioned over a region of interest on the head of the subject.

In some embodiments, the device is configured to stimulate a brain of the subject to a level below the threshold for depolarization of the neurons in the brain of the subject. In some embodiments, the magnetic field is substantially uniform, wherein the magnetic field strength varies substantially linearly, wherein the magnetic field has no gradient greater than about 5 Gauss/cm, and/or wherein the magnetic field is unidirectional. In some embodiments, the magnetic field varies according to a waveform, wherein the waveform is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec, wherein the waveform has a frequency between about 8 Hz and about 13 Hz, wherein the strength of the magnetic field is less than about 100 Gauss, and/or wherein the strength of the magnetic field is less than about 500 milli-gauss.

Provided herein is a method for treating a subject comprising: providing a Low Field Magnetic Stimulation device having a magnetic field generator that is adjusted to or is adjustable to generate a magnetic field that influences an intrinsic frequency of a specified EEG band of the subject toward a target intrinsic frequency of the specified EEG band, influences a Q-factor of an intrinsic frequency within a specified EEG band of the subject toward a target Q-factor, influences a coherence of intrinsic frequencies among multiple sites in a brain of the subject within a specified EEG band toward a target coherence value; and/or influences an EEG phase between two sites in the brain of a subject of a specified EEG frequency toward a target EEG phase of the specified EEG frequency, when the magnetic field is applied to the head of a subject.

In some embodiments, the subject is treated for about 1 minute to about 1 hour, and wherein the treatment is repeated after an interval of about 6 hours to about 14 days. In some embodiments, the magnetic field generated is below the threshold for depolarization of the neurons in the brain of the subject. In some embodiments, the magnetic field is substantially uniform, wherein the magnetic field strength varies substantially linearly, wherein the magnetic field has no gradient greater than about 5 Gauss/cm, wherein the magnetic field is unidirectional. In some embodiments, the magnetic field is applied to a diffuse area of the brain of the subject. In some embodiments, the magnetic field varies according to a waveform that is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec, wherein the waveform has a frequency between about 8 Hz and about 13 Hz, and/or wherein the strength of the magnetic field is less than about 500 milli-gauss. In some embodiments, the method increases blood flow in the cortex of the subject.

In some embodiments, the method that is effective to provide a treatment comprising improving cognitive function, improving executive function, improving academic performance, improving sports performance, improving neuropathic pain in the subject, improving a neurological disorder in the subject, improving a symptom of brain damage, and improving brain dysfunction in the subject, or improve at least one of an indication in the subject; a disorder in the subject; a symptom in the subject; a dysfunction in the subject; a characteristic in the subject; and any combination thereof.

In some embodiments, the indication is selected from the group consisting of replacement for meditation, quick nap, stress release, attention span, comprehension, memory, lowered blood pressure, increased libido, sports performance, academic performance, and any combination thereof; wherein the disorder is selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof; wherein the characteristic is selected from the group consisting of peripheral visual response, attention span, immediate reaction time (IRT), movement time (MT), simple perceptual reaction time (SPR), conflict perceptual reaction time (CPR), and any combination thereof; wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia; wherein the neurological disorder comprises at least one of a brain neurological disorder, a spinal cord disorder, a peripheral nervous system disorder, a cranial nerve disorder, an autonomic nervous system disorder, a seizure disorder, epilepsy, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome; wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage; and/or wherein the brain dysfunction comprises at least one of: aphasia, dysarthria, apraxia, agnosia, and amnesia.

Provided herein is a method for treating a subject comprising influencing the brain of the subject with a magnetic field having a specified frequency, wherein the magnetic field has a strength of less than about 100 Gauss, and wherein the specified frequency influences (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the magnetic field is generated by at least one of a Low Field Magnetic Stimulator (LFMS), a Magnetic Resonance Imager (MRI), a Transcranial Magnetic Stimulator (TMS), a Neuro-EEG Synchronization Therapy device, a picoTesla™ device, or any combination thereof.

Provided herein is a device for use in treating a subject, comprising: a Magnetic Resonance Imaging (MRI) device; wherein the MRI device is adapted to generate a magnetic field that influences (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and a controller configured to allow adjustment of a frequency of the magnetic field or to allow pulsing of the magnetic field.

In some embodiments, the magnetic field is generated by a coil configured to encircle the head of the subject, wherein the magnetic field is generated by a plurality of coils around the head of the subject, or wherein the magnetic field is generated by a coil that can be positioned over a region of interest on the head of the subject. In some embodiments, the MRI device does not detect any magnetic field. In some embodiments, the device is configured to stimulate a brain of the subject to a level below the threshold for depolarization of the neurons in the brain of the subject. In some embodiments, the magnetic field is substantially uniform, wherein the magnetic field strength varies substantially linearly, wherein the magnetic field has no gradient greater than about 5 Gauss/cm, and/or wherein the magnetic field is unidirectional.

In some embodiments, the MRI device is adapted to apply the magnetic field to a diffuse area of the brain of the subject. In some embodiments, the magnetic field varies according to a waveform, wherein the waveform is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec, wherein the waveform has a frequency between about 8 Hz and about 13 Hz, wherein the strength of the magnetic field is less than about 100 Gauss, and/or wherein the strength of the magnetic field is less than about 500 milli-gauss.

Provided herein is a method for treating a subject comprising pulsing an MRI with a wave train having a frequency that influences (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the method provides a treatment comprising improving cognitive function, improving executive function, improving academic performance, improving sports performance, improving neuropathic pain in the subject, improving a neurological disorder in the subject, improving a symptom of brain damage, and improving brain dysfunction in the subject, or improves at least one of an indication in the subject; a disorder in the subject; a symptom in the subject; a dysfunction in the subject; a characteristic in the subject; and any combination thereof.

In some embodiments, the indication is selected from the group consisting of replacement for meditation, quick nap, stress release, attention span, comprehension, memory, lowered blood pressure, increased libido, sports performance, academic performance, and any combination thereof; wherein the disorder is selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof; and/or wherein the characteristic is selected from the group consisting of peripheral visual response, attention span, immediate reaction time (IRT), movement time (MT), simple perceptual reaction time (SPR), conflict perceptual reaction time (CPR), and any combination thereof; and/or wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia; wherein the neurological disorder comprises at least one of a brain neurological disorder, a spinal cord disorder, a peripheral nervous system disorder, a cranial nerve disorder, an autonomic nervous system disorder, a seizure disorder, epilepsy, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome; wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage; and/or wherein the brain dysfunction comprises at least one of: aphasia, dysarthria, apraxia, agnosia, and amnesia.

In some embodiments, a magnetic field generated by the wave train is below the threshold for depolarization of the neurons in the brain of the subject. In some embodiments, the magnetic field is substantially uniform, wherein the magnetic field strength varies substantially linearly, wherein the magnetic field has no gradient greater than about 5 Gauss/cm, wherein the magnetic field is unidirectional. In some embodiments, the magnetic field is applied to a diffuse area of the brain of the subject. In some embodiments, the magnetic field varies according to a waveform that is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid. In some embodiments, the waveform has a period of less than about 10 msec, wherein the waveform has a frequency between about 8 Hz and about 13 Hz, wherein the strength of the magnetic field is less than about 100 Gauss, and/or wherein the strength of the magnetic field is less than about 500 milli-gauss.

INCORPORATION BY REFERENCE

All publications and patent applications mentioned in this specification are herein incorporated by reference to the same extent as if each individual publication or patent application was specifically and individually indicated to be incorporated by reference in their entirety. Incorporated publications include:

U.S. Patent Publication Number 2011/0137104 A1, "SYSTEMS AND METHODS FOR DEPRESSION TREATMENT USING NEURO-EEG SYNCHRONIZATION THERAPY", filed Nov. 11, 2010

U.S. Patent Publication Number 2011/0118536 A1, "SYSTEMS AND METHODS FOR NEURO-EEG SYNCHRONIZATION THERAPY", filed Nov. 11, 2010

U.S. Patent Publication Number 2011/0112427 A1, "SYSTEMS AND METHODS FOR NEURO-EEG SYNCHRONIZATION THERAPY", filed Nov. 9, 2010

U.S. Patent Publication Number 2011/0034822 A1, "SYSTEMS AND METHODS FOR MODULATING THE ELECTRICAL ACTIVITY OF A BRAIN USING NEURO-EEG SYNCHRONIZATION THERAPY", filed Aug. 4, 2010

U.S. Patent Publication Number 2009/0204015 A1, "Systems and Methods for Depression Treatment Using Neuro-EEG Synchronization Therapy", filed Sep. 24, 2008

U.S. Patent Publication Number 2009/0198144 A1, "Systems and Methods for Anxiety Treatment Using Neuro-EEG Synchronization Therapy", filed Sep. 24, 2008

U.S. Patent Publication Number 2009/0083071 A1, "Systems and Methods for Controlling and Billing Neuro-EEG Synchronization Therapy", filed Sep. 24, 2008

U.S. Patent Publication Number 2009/0082690 A1, "Systems and Methods for Neuro-EEG Synchronization Therapy", filed Sep. 24, 2008

BRIEF DESCRIPTION OF THE DRAWINGS

A better understanding of the features and advantages of the systems and methods provided will be obtained by reference to the following detailed description that sets forth illustrative embodiments and the accompanying drawings of which.

DETAILED DESCRIPTION OF THE INVENTION

Figure 1:
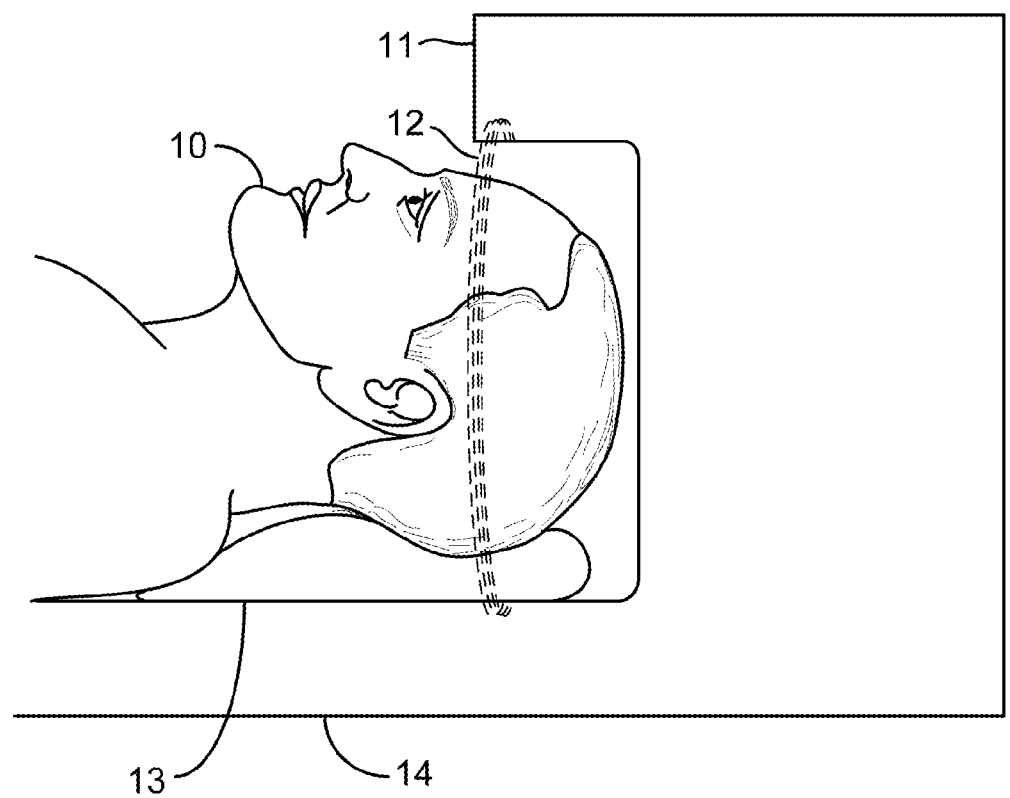
FIG. 1 shows an example of a subject receiving LFMS treatment, wherein the coil of the device encircles the head.

Since brain activity is a distributed phenomenon, conventional high-energy pulses used by rTMS that focus on a specific area of the brain are not optimal for influencing the overall frequency of the brain. Instead, it is possible to use a lower energy magnetic field applied to the entire brain to generate a similar effect. To affect the brain with a lower energy magnetic field, the stimulation may need to be applied for a longer period of time and/or be "tuned" to influence one of the brain's intrinsic frequencies.

While certain embodiments have been provided and described herein, it will be readily apparent to those skilled in the art that such embodiments are provided by way of example only. It should be understood that various alternatives to the embodiments described herein may be employed, and are part of the invention described herein.

Device

The devices described herein include Low Field Magnetic Stimulation (LFMS) devices, and/or comprise LFMS modules. In one aspect, the LFMS device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller that determines the frequency or pulsing of the device.

The devices described herein are capable of generating a magnetic field. In one aspect, the devices differ from some other devices including Magnetic Resonance Imagers (MRI), Transcranial Magnetic Stimulators (TMS), and Neuro-EEG Synchronization Therapy (NEST) devices in that LFMS produces a magnetic field of low strength. In another aspect, the devices described herein may differ from some other devices in that the devices described herein emit, but do not detect magnetic fields. This does not preclude the fact that the devices described herein may be capable of detecting magnetic fields, only the fact that in some embodiments a magnetic field is not detected and/or measured. Table 1 compares aspects of various devices. In one aspect, the LFMS devices described herein differ from the LFMS in Table 1 at least in the fact that the frequency of the methods and devices described herein is more typically less than about 100 Hz and/or tuned to an intrinsic frequency of the brain.

Described herein are various devices and/or modified devices capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof. In one embodiment, the device can include a means for controlling and/or adjusting the frequency of the device (i.e. an MRI that is pre-adjusted and/or allows for adjustment of the frequency to a target frequency, typically less than about 100 Hz). In one embodiment, the device can include a means for controlling and/or adjusting the strength of the magnetic field produced by the device (i.e. an MRI that is pre-adjusted and/or allows for adjustment of the strength to a target strength, typically less than about 100 Gauss).

TABLE 1

Example Devices

| | LFMS | MRI | NEST (NeoSync) | TMS |
|---|---|---|---|---|
| Field source | Coil (electro-magnet) | Coil (electro-magnet) | Permanent Magnet | Coil (electro-magnet) |
| Target | Whole brain | Many body parts | Whole brain | Part of brain |
| Field Strength | ~50-60 Gauss | ~1-3 Tesla | ~6k Gauss | ~3 Tesla |
| Freq | ~1800 Hz | ~1800 Hz | ~8-13 Hz (for example when influencing the alpha wave) | Various |
| Magnetic Field | Uniform magnetic field | Uniform magnetic field | (various) | High magnetic field gradient |
| Other | Emits without detecting | Emits and detects | Non-stimulating | Stimulates |

Parameters such as the frequency, magnetic field strength, and the like may be adjusted using a controller and/or user interface. In some embodiments, the device is adjustable only by an individual possessing a certain password, control device, and the like, for example only by a licensed medical professional. In other aspects, the device can adjust parameters automatically based on feedback from the subject and/or feedback from biophysical measurements of the subject, including without limitation measurements of one or more intrinsic frequencies of the subject's brain.

In one aspect described herein is a device for use in treating a subject, comprising: a Magnetic Resonance Imaging (MRI) device; wherein the MRI device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller capable of adjusting the frequency or pulsing of the device.

In one aspect described herein is a device for treating a subject comprising: a Low Field Magnetic Stimulation device capable of generating a magnetic field for one or more of the following: influencing an intrinsic frequency of a specified EEG band of the subject toward a target intrinsic frequency of the specified EEG band, for influencing a Q-factor of an intrinsic frequency within a specified EEG band of the subject toward a target Q-factor, influencing a coherence of intrinsic frequencies among multiple sites in a brain of the subject within a specified EEG band toward a target coherence value; influencing an EEG phase between two sites in the brain of a subject of a specified EEG frequency toward a target EEG phase of the specified EEG frequency; and the device is capable of applying said magnetic field to the head of the subject.

In various embodiments, the magnetic field is generated using an electromagnet, permanent magnet, or a combination thereof. In some embodiments, the permanent magnets for the methods and devices described comprise rare earth magnets such as neodymium, iron, boron or samarium cobalt magnets. In some embodiments, the permanent magnets for the methods and devices described are neodymium iron boron magnets. In some embodiments, ceramic magnets or other more powerful magnets may be utilized as they become available. In some embodiments, electromagnets may be utilized for the methods and devices described. Current can be supplied to the electromagnet by wires penetrating through the devices described and connecting to an external power source. The wires are optionally formed into a coil, optionally around a core of ferromagnetic material.

In some embodiments, the magnetic field results from a first magnetic source and a second magnetic source. In some embodiments, the first magnetic source and the second magnetic source are out of phase relative to each other. In some embodiments, the amount that the first magnetic source and the second magnetic source are out of phase relative to each other is called the magnetic phase.

In another aspect, the strength of the magnetic field can vary over time. The strength of the magnetic field can be made to vary in at least two ways. In one embodiment, a permanent magnet can be moved in a periodic manner relative to the head of the subject. The permanent magnet may comprise a north pole and a south pole, and be rotated whereby the north and south poles are alternately positioned adjacent to the head of the subject. In another embodiment, the field strength of an electromagnet can be varied over time by changing the amount of current flowing through the wires and/or coils of the electromagnet.

Figure 2:
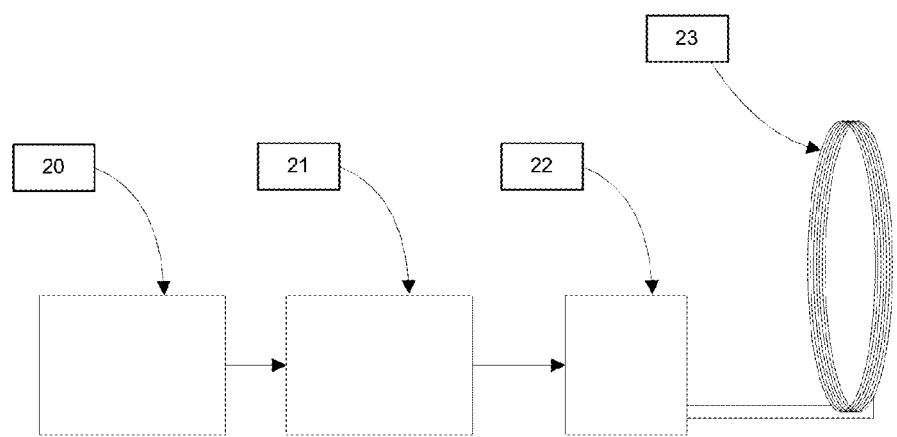
FIG. 2 shows a schematic of a LFMS device.

Directing attention to FIG. 2, shown herein is a schematic of a LFMS device. The devices described herein may comprise one or more modules. In some embodiments, the device comprises a user interface 20. The user interface is the space where interaction between an operator of the device and the device itself occurs. It can be the case where an operator is not required in all instances, only that the device has a user interface capable of interaction with an operator. The user interface can provide information regarding the operation of the device such as the strength of the magnetic field, the frequency of the change in the magnetic field, and the like. The user interface can be graphical, can be computer-based, can consist of controls such as buttons, dials, and the like, or any combination thereof. The user interface can be analog or digital. In some embodiments, the user interface provides a means to adjust and/or control parameters such as the strength of the magnetic field, the frequency of the change in the magnetic field, and the like. The user interface may include a "controller", and/or a controller can comprise a user interface.

Continuing with FIG. 2, the device may comprise a waveform generator 21. The waveform generator may be in communication with the user interface 20. The waveform generator is capable of creating an electrical waveform. Since the waveform is converted into a magnetic field that influences the brain, the waveform generator can also be called a "stimulus generator". The waveform is any waveform capable of creating a magnetic field that influences (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof. In some embodiments, the waveform generator further comprises an amplifier 22. In other embodiments, the device further comprises an amplifier 22. The amplifier is capable of modifying the waveform. The waveform can be modified in any suitable manner including the amplitude and/or strength of the waveform.

Continuing with FIG. 2, the device may comprise at least one coil 23 capable of converting the electrical waveform into a magnetic field. The coils described herein can have any suitable size, geometry, position relative to the head, be made of any material and the like suitable for generating a magnetic field capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

Directing attention to FIG. 1, shown herein is an example of a subject receiving LFMS treatment, wherein the coil of the device encircles the head. The device 11 can include a coil 12 that encircles the head of the subject 10. The device may optionally have a base 14 and/or a pillow 13 on which the head of the subject 10 rests.

Figure 7:
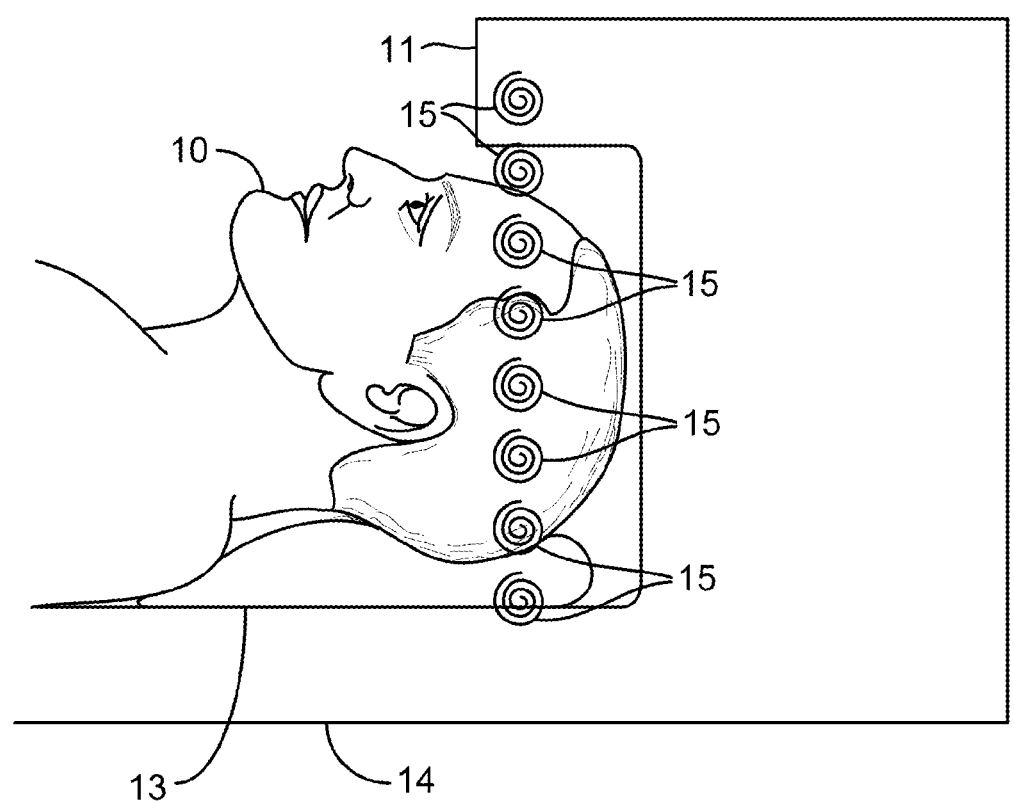
FIG. 7 shows an example of a subject receiving LFMS treatment, wherein a plurality of coils of the device are arranged around the head.

In another embodiment depicted in FIG. 7, shown herein is an example of a subject receiving LFMS treatment, wherein a plurality of coils of the device are arranged around the head. The indicative numerals 10, 11, 13 and 14 represent like elements to FIG. 1. The device may comprise a plurality of coils 15. The coils can be configured around the head of the subject in any suitable orientation. In some embodiments, a coil is configured to be positioned over a region of interest on the head of the subject. For example, the prefrontal cortex is generally thought to control mood. Therefore, in order to alter the mood of the subject, one or more coils may be positioned to influence the prefrontal cortex. The coil can be positioned to cover the prefrontal cortex of the subject in some embodiments.

FIG. 2 shows a schematic of a LFMS device. The various modules depicted in FIG. 2 work together such that the user interface can be adjusted to create a magnetic field influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the devices described can be powered with a rechargeable battery. One battery charge can be enough for one or more therapy sessions. In some embodiments, a display can indicate battery life remaining and signal when the device should be recharged.

In some embodiments, the devices described use at least one connection to a computer to allow for upload of therapy information, download of software upgrades, and to order more sessions to be allowed for the device. The connection may be a USB type of connection, or another type of connection known or contemplated. In some embodiments, the connection may be made through the use of a portable USB flash memory device or smart card that allows the physical transfer of information between a computer and the devices.

In some embodiments, the device further comprises a module capable of determining at least one brain parameter of the subject. Such a module may comprise electrodes suitable for attaching to the head of the subject and also suitable for measuring electrical activity along the scalp as is commonly done in the field of electroencephalography. The module may also comprise any suitable means for recording, interpreting, analyzing, and the like the signals measured by the electrodes.

The device as described herein may be operable to measure the EEG signal from the subject's brain prior to and/or after the application of the magnetic field to the subject. The device as described herein may comprise logic (in a computer readable format- for non-limiting example, hardware, software) that receives and records the EEG signal prior to and/or following application of the magnetic field to the subject's brain (or a portion thereof). The device as described herein may comprise logic (in a computer readable format) that determines the intrinsic frequency of a specified EEG band of the subject using the EEG signal prior to and/or following application of the magnetic field to the subject's brain (or a portion thereof). The device as described herein may comprise logic (in a computer readable format) that determines the Q-factor of an intrinsic frequency of a specified EEG band of the subject using the EEG signal prior to and/or following application of the magnetic field to the subject's brain (or a portion thereof). The device as described herein may comprise logic (in a computer readable format) that determines the coherence of the intrinsic frequencies of a specified EEG band of the subject measured at multiple brain locations. The device as described herein may comprise logic (in a computer readable format) that determines the phase of the intrinsic frequencies of a specified EEG band of the subject measured at multiple brain locations.

In some embodiments, the methods include measuring at least one brain parameter of the subject. Thus, the devices described herein may contain a module capable of measuring at least one brain parameter of the subject. Such methods and/or device modules are now described in more detail below.

Device Modules and/or Methods for Measuring Brain Parameters

Described herein are methods for treating a subject. In some embodiments, at least one brain parameter is measured in the subject. The "brain parameter" may comprise an intrinsic frequency, an intrinsic Q-factor, an intrinsic coherence, an intrinsic EEG phase, and any combination thereof. Methods for measuring brain parameters are now described in more detail. It should be understood that device modules capable of measuring brain parameters are also encompassed by the present invention.

In some embodiments of the methods described herein, the method or methods may comprise locating a first electrode operable to detect electrical brain activity on the subject in an area of low electrical resistivity on a subject. In some embodiments of the methods described herein, the method or methods may comprise locating a first electrode operable to detect electrical brain activity on the subject in an area with substantially no electrical impulse interference on a subject. In some embodiments of the methods described herein, the method or methods may comprise locating a first electrode operable to detect electrical brain activity on the subject in an area having substantially no electrical impulse interference. In some embodiments of the methods described herein, the method or methods may comprise locating a first electrode operable to detect electrical brain activity on the subject in a location having substantially no muscle activity. The method or methods may further comprise locating a second electrode operable to detect a reference signal on the subject. The method or methods may further comprise determining the intrinsic frequency from: the electrical brain activity detected by the first electrode, and the reference signal detected by the second electrode.

In some embodiments of the methods described herein, the method or methods may comprise locating a first electrode operable to detect electrical brain activity on the subject in at least a portion of the ear canal of the subject. The method or methods may further comprise locating a second electrode operable to detect a reference signal on the subject. The method or methods may further comprise determining the intrinsic frequency from the electrical brain activity detected by the first electrode and the reference signal detected by the second electrode.

The method or methods described herein may comprise applying conductive gel to the area of low electrical resistivity on a subject (i.e. the location at which the first electrode is placed). The method or methods described herein may comprise applying conductive gel to the area having substantially no electrical impulse interference on a subject (i.e. the location at which the first electrode is placed). The method or methods described herein may comprise applying conductive gel to the area having substantially no muscle activity (i.e. the location at which the first electrode is placed). Alternatively, or in addition to the applying the gel, the method may comprise shaping the first electrode to fit the area at which the first electrode is placed, for non-limiting example, the portion of the ear canal or the portion of the nasal cavity in which the first electrode is placed. The electrode may be pre-shaped to generally fit the intended anatomical location of electrode placement, or the electrode may be shaped in-situ to fit the specific individual's anatomical location of electrode placement. The method may comprise shaping the electrode to fit an anatomical location (for example, the area at which the first electrode is to be placed). The method may comprise providing an electrode that fits an anatomical location (for example, the area at which the first electrode is to be placed). The first electrode may come in multiple sizes to accommodate a range of subjects' anatomy. The first electrode may be configured such that the subject may place the electrode in the area having substantially no electrical impulse interference without assistance from, for non-limiting example, a second person, a trained EEG technician, or a medical professional.

The method or methods described herein may comprise placing the first electrode in a location having substantially no electrical impulse interference or a location having substantially no muscle activity. The area having substantially no muscle activity may naturally have substantially no muscle activity. The method or methods described herein may comprise relaxing the area of the subject at which the first electrode is placed by a muscle relaxation means such as by, for non-limiting example, injecting with a substance that relaxes the muscles in the area, applying a topical substance that relaxes the muscles in the area, and/or by providing an ingestible muscle relaxation substance to the subject that relaxes the muscles in the area. The method or methods described herein may comprise paralyzing the area of the subject at which the first electrode is placed by a muscle paralysis means such as by, for non-limiting example, and/or injecting with a substance that substantially paralyzes the muscles in the area, applying a topical substance that substantially paralyzes the muscles in the area.

While an anatomical location of substantially no electrical impulse interference, and/or a location having substantially no muscle activity (but where brain activity may be measured) may provide a clearer EEG signal resulting in less noise and reduced resistivity from the skull, nevertheless, the methods provided herein may comprise placing the first electrode on the scalp (either directly, and/or with hair between the scalp and the electrode). The methods provided herein may comprise placing a plurality of electrodes on the scalp for coherence measurement, intrinsic frequency measurement, and/or Q-factor measurement. The methods provided herein may comprise filtering from the signal (or signals) received from the EEG electrodes noise from scalp movement and/or resistivity from the skull. The methods provided herein may comprise smoothing the signal curve received and/or determined from the EEG electrodes. The methods provided herein may comprise determining from multiple signal recordings: a coherence measurement, an intrinsic frequency measurement, and/or a Q-factor measurement using any of the EEG recording means noted herein. An EEG electrode cap may be used, and signals from one or more electrodes of the cap may be used as described herein to determine an intrinsic frequency, a Q-factor, or coherence.

The area of the scalp upon which the first EEG electrode (or the plurality of electrodes) is/are placed may be induced to have less muscle activity, or it may naturally have less muscle activity than other areas on the scalp. Inducing less muscle activity in the area of the scalp may be achieved in various ways. For non-limiting example, the methods may comprise relaxing the area where the first electrode is placed, for non-limiting example, by injecting the area with a substance that relaxes (and/or paralyzes) the muscles in the area, applying a topical substance that relaxes (and/or paralyzes) the muscles in the area, and/or by providing an ingestible muscle relaxation substance that relaxes the muscles in the area.

In some embodiments, the method comprises placing a second electrode operable to detect a reference signal, wherein the second electrode is a ground reference. The method may comprise attaching an ear clip electrode to, for non-limiting example, a subject's earlobe. The ear clip may be removable. The method may comprise attaching the second electrode to a location showing substantially no EEG activity.

Measuring the EEG signal from the subject's brain (i.e. measuring EEG data of the subject) may be done prior to and/or after the application of the magnetic field to the subject. The method may comprise receiving the EEG signals (i.e. receiving the reference signal from the reference electrode and receiving the brain activity from the first electrode) prior to application of the magnetic field to the subject's brain (or a portion thereof). The method may comprise recording the EEG signals prior to application of the magnetic field to the subject's brain (or a portion thereof). The EEG signals (i.e. receiving the reference signal from the reference electrode and receiving the brain activity from the first electrode) received and/or recorded prior to application of the magnetic field to the subject's brain (or a portion thereof) may be used in determining at least one of the intrinsic frequency of a specified EEG band of the subject, the Q-factor of an intrinsic frequency of a specified EEG band of the subject, the phase of the intrinsic frequencies of a specified EEG band of the subject, and the coherence of the intrinsic frequencies of a specified EEG band of the subject measured at multiple brain locations. The method may comprise receiving the EEG signals (i.e. receiving the reference signal from the reference electrode and receiving the brain activity from the first electrode) following (or after) application of the magnetic field to the subject's brain (or a portion thereof). The method may comprise recording the EEG signals (i.e. the reference signal from the reference electrode and the brain activity from the first electrode) following or after application of the magnetic field to the subject's brain (or a portion thereof). The EEG signals received and/or recorded (i.e. the reference signal from the reference electrode and the brain activity from the first electrode) following (or after) application of the magnetic field to the subject's brain (or a portion thereof) may be used in determining at least one of the post-treatment intrinsic frequency of a specified EEG band of the subject, the post-treatment Q-factor of an intrinsic frequency of a specified EEG band of the subject, the post-treatment phase of the intrinsic frequencies of a specified EEG band of the subject, and the post-treatment coherence of the intrinsic frequencies of a specified EEG band of the subject measured at multiple brain locations. Determining the intrinsic frequency may comprise removing the reference signal detected by the second electrode from the electrical brain activity detected by the first electrode. Determining the Q-factor of an intrinsic frequency of the specified EEG band comprises ascertaining the Q-factor from the electrical brain activity detected by the first electrode and the reference signal detected by the second electrode by removing the reference signal detected by the second electrode from the electrical brain activity detected by the first electrode and calculating the Q-factor from the intrinsic frequency of and the $\Delta f$ as shown in FIG. 4.

Figure 4:
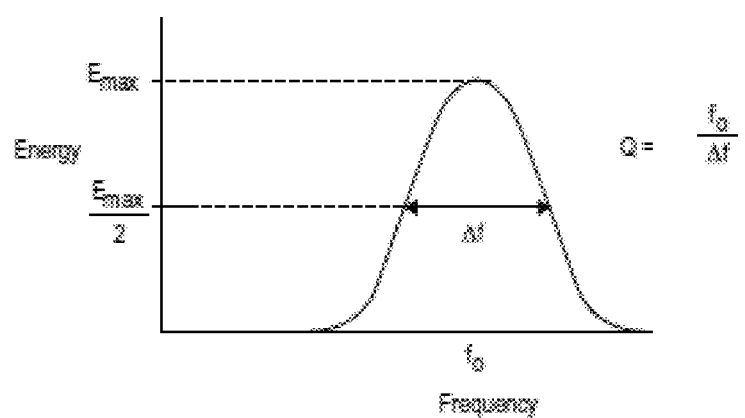
FIG. 4 shows an example of the Q-factor as used in this invention.

FIG. 4 shows an example of the Q-factor as used in this invention. The figure shows a sample graph of the frequency distribution of the energy of an EEG signal. It can be seen that a frequency range, $\Delta f$ can be defined as the frequency bandwidth for which the energy is above one-half the peak energy. The frequency $f_0$ is defined as the intrinsic frequency in the specified band. The Q-factor is defined as the ratio of $f_0/\Delta f$. As can be seen, when $\Delta f$ decreases for a given $f_0$, the Q-factor will increase. This can occur when the peak energy $E_{max}$ of the signal increases or when the bandwidth of the EEG signal decreases.

In some embodiments, the EEG electrodes are used to measure the brain waves of the subject continuously for a specified period of time. In some embodiments the specified period of time is for non-limiting example, at least about one hour, at least about 45 minutes, at least about 40 minutes, at least about 30 minutes, at least about 20 minutes, at least about 15 minutes, at least about 10 minutes, at least about 5 minutes, at least about 1 minute, at least 30 seconds, at least about 10 seconds, at least about 5 seconds, and at least about 1 second. The term "about" when referring to the specified period of time of use of the EEG electrodes to measure brain waves can mean variation of, for example, 1 minute to 5 minutes, 30 seconds to 1 minute, 15 seconds to 30 seconds, 5 seconds to 15 seconds, 1 second to 10 seconds, 1 second to 5 seconds, 0.5 seconds to 1 second, and 0.1 seconds to 0.5 second.

Described herein are methods for measuring brain parameters comprising placing a first electrode on the back of the head of the subject, placing a second electrode on the front of the head of the subject, placing a ground electrode on the subject, connecting the electrodes to a device, and measuring the brain parameter with the electrodes. In one embodiment, the first electrode is a sensing electrode and the second electrode is a reference electrode.

Figure 8:
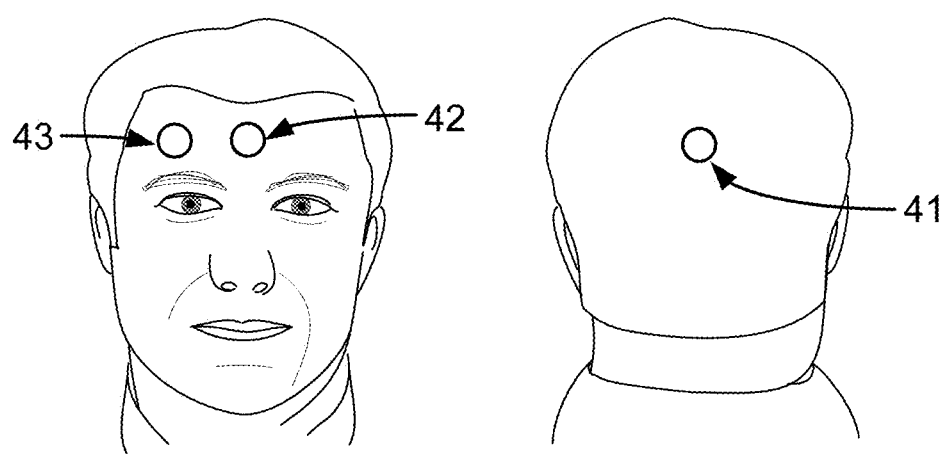
FIG. 8 depicts an exemplary placement of electrodes on the scalp of the subject for the measurement of one or more brain parameters.

Directing attention now to FIG. 8, depicted herein is an exemplary placement of electrodes on the scalp of a subject for measurement of one or more brain parameters. The first electrode 41 may be placed on the back of the head above the occipital region and/or approximately 1 inch above the inion protrusion. The second electrode 42 may be placed approximately one inch above the bridge between the eyebrows and/or directly in front of the pre-frontal cortex. The reference electrode 43 may be placed on the front of the head of the subject as well.

In some embodiments, the patient's brain parameter may be determined by the device described herein. In some embodiments, the patient's brain parameter is entered into the device described herein. In yet more embodiments, the brain parameter is entered through the user interface, is entered from external memory device, or is entered from a network connection.

Methods

Described herein are methods for treating a subject. In one aspect the method includes influencing the brain of the subject with a magnetic field having a specified frequency. In some embodiments, the specified frequency is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the magnetic field has a strength of less than about 100 Gauss. Thus in one aspect, the methods described herein may differ from some other methods including Magnetic Resonance Imaging (MRI), Transcranial Magnetic Stimulation (TMS), and Neuro-EEG Synchronization Therapy (NEST) that these methods generally use a magnetic field strength of at least about 6,000 Gauss, and often at least 1 Tesla. A picoTesla™ device has a field strength of less than about 100 Gauss, so is a suitable device for practicing the methods of the invention.

Low Field Magnetic Stimulation (LFMS) devices, including those described herein generally produce a magnetic field having a strength between about 50-60 Gauss and are suitable devices for practicing the methods of the invention. In one embodiment, the method for treating a subject comprises adjusting the output of a Low Field Magnetic Stimulation device to generate a magnetic field for one or more of the following: (i) influencing an intrinsic frequency of a specified EEG band of the subject toward a target intrinsic frequency of the specified EEG band, (ii) for influencing a Q-factor of an intrinsic frequency within a specified EEG band of the subject toward a target Q-factor, (iii) influencing a coherence of intrinsic frequencies among multiple sites in a brain of the subject within a specified EEG band toward a target coherence value; (iv) influencing an EEG phase between two sites in the brain of a subject of a specified EEG frequency toward a target EEG phase of the specified EEG frequency; and applying said magnetic field to a head of the subject. In some embodiments, the EEG band is the intrinsic alpha frequency which is generally at a frequency of about 8-13 Hz. The LFMS in some embodiments is close to the head of the subject. In some embodiments the LFMS, or a portion thereof, is touching the subject. In some embodiments the LFMS, or a portion thereof, is touching the head of the subject.

In another embodiment, the method for treating a subject comprises: adjusting an intrinsic frequency of the subject by applying a magnetic field generated from a Low Field Magnetic Stimulation device to the head of the subject, wherein the magnetic field comprises at least one of (a) a single target frequency; (b) a plurality of frequencies within a specified EEG band; and (c) an intrinsic frequency of a brain of the subject within a specified EEG band.

In another aspect are methods of altering an intrinsic frequency of a brain of a subject within a specified EEG band, comprising: (a) determining the intrinsic frequency of the subject within the specified EEG band; (b) comparing the intrinsic frequency from step (a) to an average intrinsic frequency of a control group; (c) if the intrinsic frequency from step (a) is higher than the average intrinsic frequency of the control group, shifting down the intrinsic frequency of the subject by applying a specific magnetic field generated from a LFMS device to a head of the subject, wherein said specific magnetic field has a frequency lower than the intrinsic frequency of the subject; and (d) if the intrinsic frequency from step (a) is lower than the average intrinsic frequency of the control group, shifting up the intrinsic frequency of the subject by applying a specific magnetic field generated from a LFMS device to a head of the subject, wherein said specific magnetic field has a frequency higher than the intrinsic frequency of the subject. The LFMS in some embodiments is close to the head of the subject. In some embodiments the LFMS, or a portion thereof, is touching the subject. In some embodiments the LFMS, or a portion thereof, is touching the head of the subject.

In another aspect are methods of modulating the electrical activity of a brain in a subject in need thereof, comprising: (a) adjusting output of a magnetic field for influencing a Q-factor, a measure of frequency selectivity of a specified EEG band, of the subject toward a target Q-factor of the band; and (b) applying said magnetic field generated from a LFMS device to a head of the subject. In another aspect are methods of modulating the electrical activity of a brain in a subject in need thereof, comprising: determining the Q-factor of the intrinsic frequency within the specified EEG band of the subject; comparing the Q-factor of the intrinsic frequency from step (a) to an average Q-factor of the intrinsic frequency of a control group; if the Q-factor of the intrinsic frequency from step (a) is higher than the average Q-factor of the intrinsic frequency of the control group, tuning down the Q-factor of the intrinsic frequency of the subject by applying a magnetic field with a plurality of frequencies or with a single target frequency generated from a LFMS device to a head of the subject; and if the Q-factor of the intrinsic frequency from step (a) is lower than the average Q-factor of the intrinsic frequency of the control group, tuning up the Q-factor of the intrinsic frequency of the subject by applying a magnetic field with a target frequency generated from a LFMS device to a head of the subject. The LFMS in some embodiments is close to the head of the subject. In some embodiments the LFMS, or a portion thereof, is touching the subject. In some embodiments the LFMS, or a portion thereof, is touching the head of the subject.

In another aspect are methods adjusting output of a magnetic field for influencing a coherence of intrinsic frequencies among multiple sites in a brain of the subject within a specified EEG band toward a target coherence value comprising: determining the coherence value of the intrinsic frequencies among multiple locations throughout a scalp of the subject; comparing the coherence value from step (a) to an average coherence value of a control group; if the coherence value from step (a) is higher than the average coherence value of the control group, lowering the coherence value of the subject by applying at least two asynchronous magnetic fields generated from a LFMS device to a head of the subject; if the coherence value from step (a) is lower than the average coherence value of the control group, raising the coherence value of the subject by applying at least one synchronized magnetic field generated from a LFMS device to a head of the subject. The LFMS in some embodiments is close to the head of the subject. In some embodiments the LFMS, or a portion thereof, is touching the subject. In some embodiments the LFMS, or a portion thereof, is touching the head of the subject.

In another aspect are methods for influencing an EEG phase of a specified EEG frequency between multiple locations of a brain of a subject, comprising: (a) determining the EEG phase between the at least two locations measured on the head of the subject; (b) comparing the EEG phase from step (a) to an average EEG phase of a control group; and (c) applying a magnetic field generated from a LFMS device to a head of the subject wherein applying the magnetic field influences the determined EEG phase toward the average EEG phase of a control group. The LFMS in some embodiments is close to the head of the subject. In some embodiments the LFMS, or a portion thereof, is touching the subject. In some embodiments the LFMS, or a portion thereof, is touching the head of the subject.

In some methods, the brain is influenced with a Magnetic Resonance Imager (MRI), a Transcranial Magnetic Stimulator (TMS), a Neuro-EEG Synchronization Therapy (NEST) device, or any combination thereof. In some embodiments, the strength of the magnetic field produced by these devices may be reduced to a suitable level such that the effective field strength at the subject's head is less than about 100 Gauss. In some embodiments, the strength of the magnetic field produced by these devices may be reduced to a suitable level such that the effective field strength at the subject's head is less than about 1 Tesla. In some embodiments, the strength of the magnetic field produced by these devices may be reduced to a suitable level such that the effective field strength at the subject's head is less than about 9000 Gauss. In some embodiments, the strength of the magnetic field produced by these devices may be reduced to a suitable level such that the effective field strength at the subject's head is less than about 8000 Gauss. In some embodiments, the strength of the magnetic field produced by these devices may be reduced to a suitable level such that the effective field strength at the subject's head is less than about 7000 Gauss. In some embodiments, the strength of the magnetic field produced by these devices may be reduced to a suitable level such that the effective field strength at the subject's head is about 6000 Gauss. In some embodiments, the strength of the magnetic field produced by these devices may be reduced to a suitable level such that the effective field strength at the subject's head is about 5000 Gauss. In some embodiments, the strength of the magnetic field produced by these devices may be reduced to a suitable level such that the effective field strength at the subject's head is about 4000 Gauss. In some embodiments, the strength of the magnetic field produced by these devices may be reduced to a suitable level such that the effective field strength at the subject's head is about 3000 Gauss. In some embodiments, the strength of the magnetic field produced by these devices may be reduced to a suitable level such that the effective field strength at the subject's head is about 2000 Gauss. In some embodiments, the strength of the magnetic field produced by these devices may be reduced to a suitable level such that the effective field strength at the subject's head is about 1000 Gauss. For non-limiting example, the of the magnetic field produced by these devices may be reduced by inserting shielding between the device and the subject's head. In another non-limiting example, the magnetic field produced by these devices may be reduced by lowering the magnitude of the electric current through the coil.

Typical MRI, and LFMS or certain other devices do not have an adjustable frequency and/or may not be set to a frequency suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof. For example, MRI's are generally designed to emit a magnetic field with a frequency of about 1800 Hz. An MRI alternates between emitting a magnetic field and detecting a magnetic field for the purposes of generating an image of material subjected to the emitted magnetic field.

Nevertheless, in some embodiments an MRI, and/or an LFMS may be operated in a manner such that it is suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

For non-limiting example, in some embodiments, the MRI is modified to emit, but not detect magnetic fields.

For non-limiting example, the method comprises pulsing the MRI to generate a wave train having a frequency capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

Figure 3:
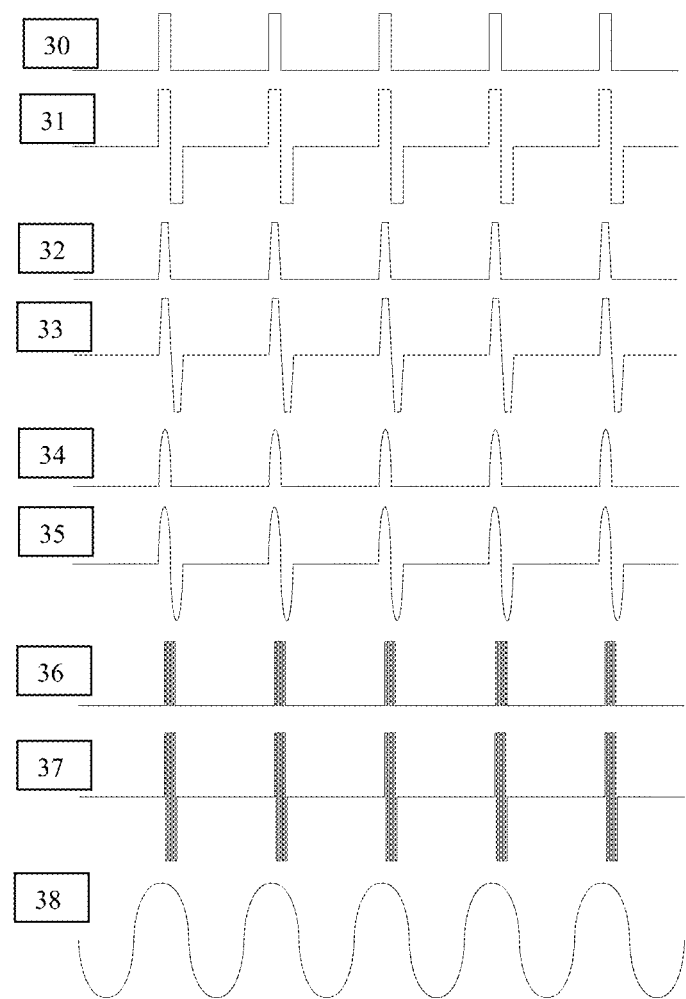
FIG. 3 shows exemplary waveforms suitable for the methods described herein.

FIG. 3 shows exemplary waveforms suitable for the methods described herein. Exemplary waveforms include the wave trains depicted in FIG. 3. Wave trains 36 and 37 show bursts of 1800 Hz magnetic fields produced with substantially no magnetic field produced between the bursts. The time period between the bursts is suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

Likewise, a device such as a TMS or a NEST device may be used in a manner which similarly pulses a high frequency wave train, e.g. bursts of >50 Hz which occur at the target frequency or frequencies (for example if hopping frequencies), similar to the wave train as shown in FIG. 3.

For non-limiting example, the method comprises including a controller as part of the MRI device which allows adjustment of the frequency emitted by the MRI or the LFMS to generate a magnetic field at a frequency capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof. The frequency may be the IAF, or another frequency as noted herein such as a target frequency and/or the frequency of a person or persons not having the condition, disease, or symptom which is desired to be reduced, eliminated, or treated, or may be the frequency of a person or persons having the aspect which is desired to be improved, honed, or increased, or a hopping set of frequencies, or may be a frequency other than 1800 Hz which is pulsed at the appropriate frequency to generate a wave train as similarly shown in FIG. 3.

Details of Treatments

In some embodiments, described herein are methods of treating a subject. The treatment may be performed for any length of time suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the subject is treated for about 1 minute, about 5 minutes, about 15 minutes, about 30 minutes, about 45 minutes, about 60 minutes, about 90 minutes, about 2 hours, or about 4 hours. In some embodiments, the subject is treated for at least about 1 minute, at least about 5 minutes, at least about 15 minutes, at least about 30 minutes, at least about 45 minutes, at least about 60 minutes, at least about 90 minutes, at least about 2 hours, or at least about 4 hours. In some embodiments, the subject is treated for about 1 minute to about 30 minutes, for about 30 minutes to about 40 minutes, for about 15 minutes to about 60 minutes, for about 25 minutes to about 45 minutes, and the like.

The treatment may be repeated after any amount of time suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In some embodiments, the treatment is repeated after an interval of about 1 hour, about 6 hours, about 12 hours, about 24 hours, about 2 days, about 7 days, about 14 days, or about 30 days. In some embodiments, the treatment is repeated after an interval of at most about 1 hour, at most about 6 hours, at most about 12 hours, at most about 24 hours, at most about 2 days, at most about 7 days, at most about 14 days, or at most about 30 days. In some embodiments, the treatment is repeated after an interval of between about 1 hour and about 6 hours, between about 12 hours and about 24 hours, between about 1 day and about 5 days, between about 7 days and about 14 days, and the like.

In some embodiments, the subject is treated substantially all the time. In these embodiments, the device is preferably configured to be worn on the head with a portable source of power.

EEG Bands and Target Parameters Thereof.

In some embodiments, the methods or devices described herein adjust the output of a Low Field Magnetic Stimulation device to generate a magnetic field for one or more of the following: (i) influencing an intrinsic frequency of a specified EEG band of the subject toward a target intrinsic frequency of the specified EEG band, (ii) for influencing a Q-factor of an intrinsic frequency within a specified EEG band of the subject toward a target Q-factor, (iii) influencing a coherence of intrinsic frequencies among multiple sites in a brain of the subject within a specified EEG band toward a target coherence value; (iv) influencing an EEG phase between two sites in the brain of a subject of a specified EEG frequency toward a target EEG phase of the specified EEG frequency; and apply the magnetic field to a head of the subject. The LFMS in some embodiments is close to the head of the subject. In some embodiments the LFMS, or a portion thereof, is touching the subject. In some embodiments the LFMS, or a portion thereof, is touching the head of the subject.

The specified EEG band may be alpha wave, a beta wave, a gamma wave, a mu wave, a delta wave, a theta wave, or any combination thereof. Table 2 lists exemplary EEG bands and the characteristic frequencies at which the band is generally found.

TABLE 2

Exemplary EEG bands

| EEG Band | Frequency (Hz) |
| --- | --- |
| Alpha | 8-13 |
| Beta | 13-30 |
| Gamma | 30-100+ |
| Delta | up to 4 |
| Theta | 4-8 |
| Mu | 8-13 |

In some embodiments, the intrinsic frequency of the subject is an intrinsic alpha frequency (IAF) of a brain of the subject. In some embodiments, alpha EEG of a brain of a subject can be critical in normal cognitive processes and the desynchronization of alpha activity can play a pathophysiological role in the neurological disorder listed above. In some embodiments, the therapy using methods or systems described lasts for about 20 minutes, is very gentle, and unnoticeable to the subject. In some embodiments, the quantifiable change in alpha frequency can be seen clearly following the therapy session, and the patient may have an immediate reduction in symptoms. The therapy using methods or systems described can be mild enough to be used every day or as needed. The therapy using methods or systems described does not have to involve any medication whatsoever.

Figure 5:
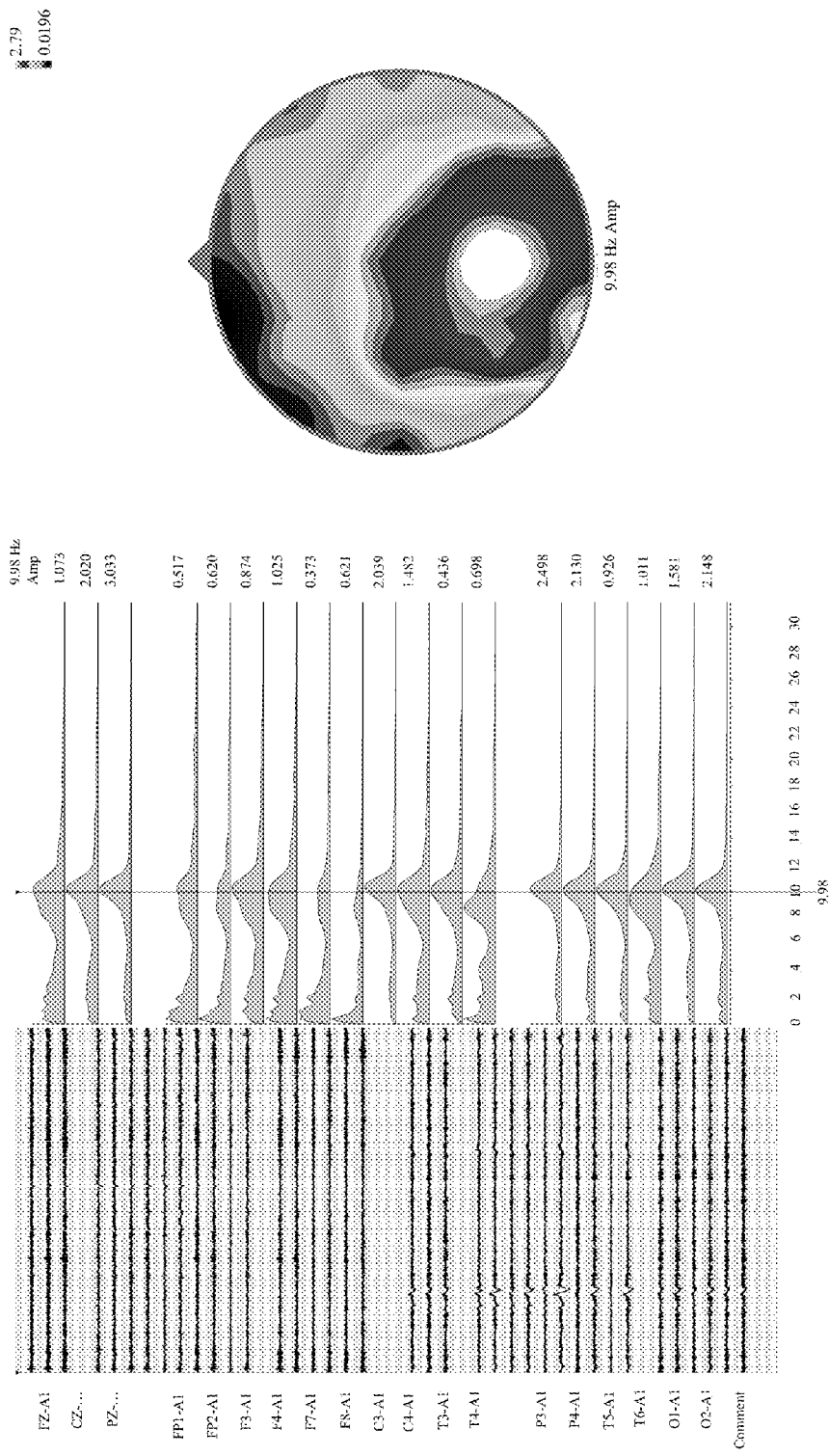
FIG. 5 shows a sample EEG segment for a subject before therapy is delivered.

FIG. 5 shows a sample EEG segment for a subject having depression before therapy is delivered. The block on the left shows a time series EEG while the subject is sitting at rest with eyes closed. The overall vertical identifiers show electrode placements (according to standard EEG placement schemes), and readings therefor in the left block graphs taken over time. From bottom to top, the electrode placement identifiers are: Comment, O2-A1, O1-A1, T6-A1, T5-A1, P4-A1, P3-A1, T4-A1, T3-A1, C4-A1, C3-A1, F8-A1, F7-A1, F4-A1, F3-A1, FP2-A1, FP1-A1, PZ-..., CZ-..., and FZ-A1, respectively. In the left block, the horizontal axis of each plot is measured in seconds and the vertical axis is measured in mV. The block in the center shows the energy across the frequency spectrum for the sampled EEG (i.e. the Fourier transform). The horizontal axis ranges from 0 Hz to 30 Hz in 2 Hz increments. The vertical line drawn through the peaks is at the subject's intrinsic alpha frequency which, in this figure for this subject, is centered at 9.98 Hz. The maximum energies detected at the IAF (9.98 Hz) for the subject are provided to the right of the center block. Again, these amplitudes represent the maximum energy measured at 9.98 Hz for the subject prior to treatment. From bottom to top, the amplitudes for each plotted curve are 2.148, 1.581, 1.011, 0.926, 2.130, 2.498, 0.698, 0.436, 1.482, 2.039, 0.621, 0.373, 1.025, 0.874, 0.620, 0.517, 3.033, 2.020, and 1.073, respectively. The circle at the right shows the distribution of EEG energy at the intrinsic alpha frequency (9.98 Hz) throughout the head, looking down on the top of the subject's head. In this view, the subject is facing the top of the page (eyes directed in the direction of the arrow at the top of the circle). The shading is based on the Fourier transform magnitude at the alpha frequency. There is a wide range of energies throughout the brain with the lowest levels represented by the darkest shading along the upper left edge of the circle and the highest levels at the white circle just below center.

Figure 6:
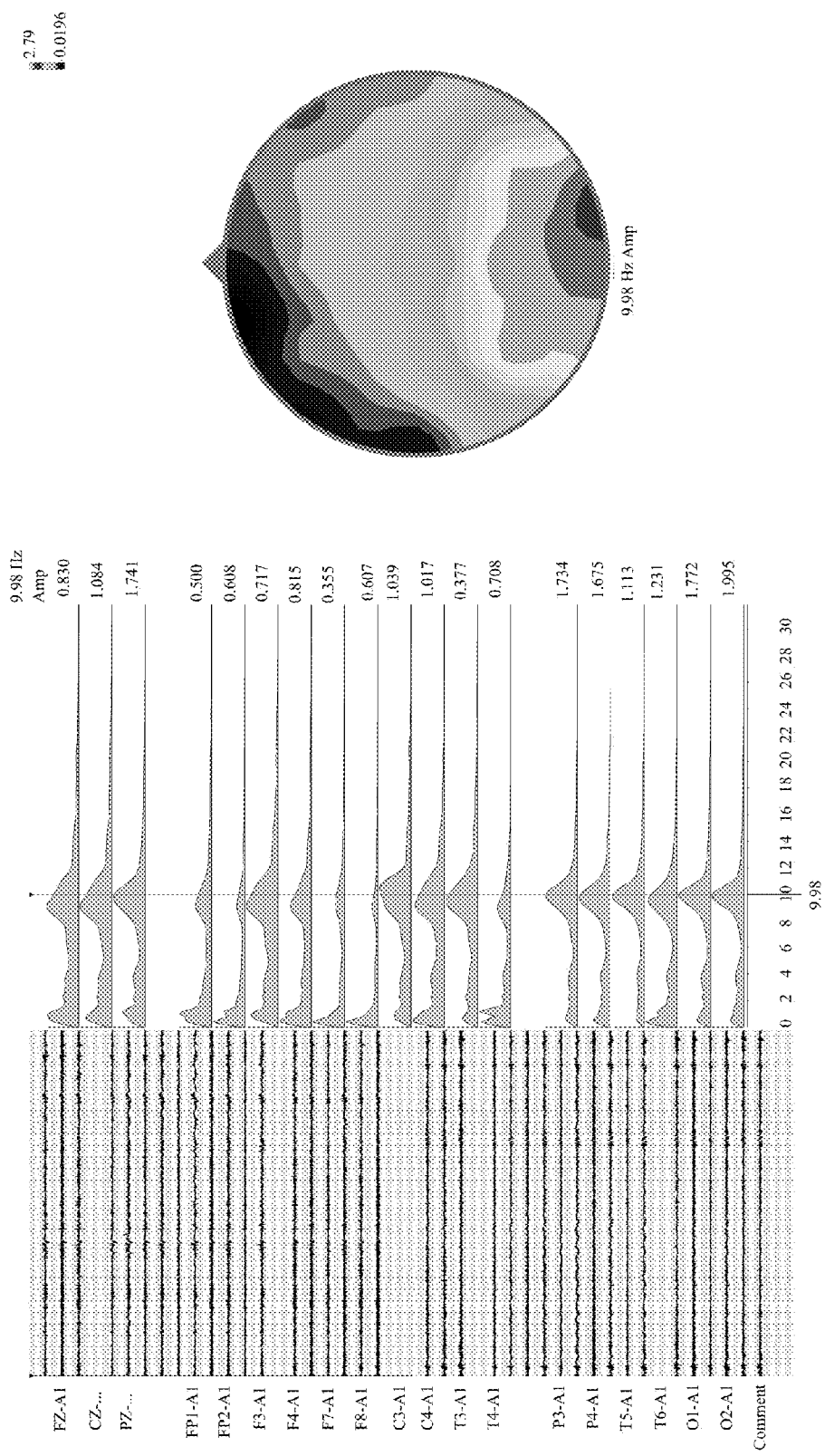
FIG. 6 shows a sample EEG segment for a subject immediately following sTMS therapy.

FIG. 6 is similar to FIG. 5, except the EEG was sampled immediately following sTMS therapy. The circle at the right shows the distribution of EEG energy at the intrinsic alpha frequency (9.98 Hz) throughout the head, looking down on the top of the subject's head. In this view, the subject is facing the top of the page (eyes directed in the direction of the arrow at the top of the circle). The shading is based on the Fourier transform magnitude at the alpha frequency. From the circle representation on the right, it can be seen that the distribution of energy at the intrinsic alpha frequency measured prior to treatment (in this subject, centered at 9.98 Hz) throughout the head is more uniform, though the majority of energy is still concentrated at the back of the brain. This subject expressed reduced depression symptoms following treatment. The depression symptoms are as noted elsewhere herein. As with FIG. 5, the block on the left in FIG. 6 shows a time series EEG while the subject is sitting at rest with eyes closed. The overall vertical identifiers of the left block show electrode placements (according to standard EEG placement schemes), and readings therefor in the left block graphs taken over time. From bottom to top, the electrode placement identifiers are: Comment, O2-A1, O1-A1, T6-A1, T5-A1, P4-A1, P3-A1, T4-A1, T3-A1, C4-A1, C3-A1, F8-A1, F7-A1, F4-A1, F3-A1, FP2-A1, FP1-A1, PZ-..., CZ-..., and FZ-A1, respectively. In the left block, the horizontal axis of each plot is measured in seconds and the vertical axis is measured in mV. The block in the center of FIG. 6 shows the energy across the frequency spectrum for the sampled EEG (i.e. the Fourier transform). The horizontal axis ranges from 0 Hz to 30 Hz in 2 Hz increments. The vertical line drawn through the peaks is at the subject's intrinsic alpha frequency which, in this figure for this subject, is centered at 9.98 Hz. The maximum energies detected at the IAF (9.98 Hz) for the subject are provided to the right of the center block. Again, these amplitudes represent the maximum energy measured at 9.98 Hz for the subject following treatment. From bottom to top, the amplitudes for each plotted curve are 1.995, 1.772, 1.231, 1.113, 1.675, 1.734, 0.708, 0.377, 1.017, 1.039, 0.607, 0.355, 0.815, 0.717, 0.608, 0.200, 1.741, 1.084, and 0.830, respectively.

In some embodiments, the methods or devices described herein adjust the output of a Low Field Magnetic Stimulation device to generate a magnetic field for influencing an intrinsic frequency of a specified EEG band of the subject toward a target intrinsic frequency of the specified EEG band. The target intrinsic frequency may be any one or more of: the subject's intrinsic frequency; the intrinsic frequency of an individual having a disorder, a disease, a deficient mental characteristic, or any combination thereof; the intrinsic frequency of an individual not having the disorder, the disease, the deficient mental characteristic, or any combination thereof; the average intrinsic frequency of a population of individuals having a disorder, a disease, a deficient mental characteristic, or any combination thereof; and the average intrinsic frequency of a population of individuals not having the disorder, the disease, the deficient mental characteristic, or any combination thereof.

In some embodiments, influencing an intrinsic frequency may include providing a magnetic field having a target frequency having no variation (standard of deviation around the target frequency is 0). In some embodiments, influencing an intrinsic frequency may include providing a magnetic field having a target frequency plus or minus at most 1% of the target frequency. In some embodiments, influencing an intrinsic frequency may include providing a magnetic field having a target frequency plus or minus at most 5% of the target frequency. In some embodiments, influencing an intrinsic frequency may include providing a magnetic field having a target frequency plus or minus at most 10% of the target frequency. In some embodiments, influencing an intrinsic frequency may include providing a magnetic field having a target frequency plus or minus at most 10% of the target frequency. In some embodiments, influencing an intrinsic frequency may include providing a magnetic field having a target frequency plus or minus at most 15% of the target frequency. In some embodiments, influencing an intrinsic frequency may include providing a magnetic field having a target frequency plus or minus at most 20% of the target frequency.

In some embodiments, the methods or devices described herein adjust the output of a Low Field Magnetic Stimulation device to generate a magnetic field for influencing a Q-factor of an intrinsic frequency within a specified EEG band of the subject toward a target Q-factor. The target Q-factor may be any one or more of: the subject's intrinsic Q-factor; the intrinsic Q-factor of an individual having a disorder, a disease, a deficient mental characteristic, or any combination thereof; the intrinsic Q-factor of an individual not having the disorder, the disease, the deficient mental characteristic, or any combination thereof; the average intrinsic Q-factor of a population of individuals having a disorder, a disease, a deficient mental characteristic, or any combination thereof; and the average intrinsic Q-factor of a population of individuals not having the disorder, the disease, the deficient mental characteristic, or any combination thereof.

In some embodiments of the methods, a controlled waveform is used to influence a Q-factor of an intrinsic frequency of a patient's brain. FIG. 4 shows an example of the Q-factor as used in this invention. The figure shows a sample graph of the frequency distribution of the energy of an EEG signal. It can be seen that a frequency range, $\Delta f$ can be defined as the frequency bandwidth for which the energy is above one-half the peak energy. The frequency $f_0$ is defined as the intrinsic frequency in the specified band. The Q-factor is defined as the ratio of $f_0/\Delta f$. As can be seen, when $\Delta F$ decreases for a given $f_0$, the Q-factor will increase. This can occur when the peak energy $E_{max}$ of the signal increases or when the bandwidth of the EEG signal decreases.

In some embodiments, the methods or devices described herein adjust the output of a Low Field Magnetic Stimulation device to generate a magnetic field for influencing a coherence of intrinsic frequencies among multiple sites in a brain of the subject within a specified EEG band toward a target coherence value. The target coherence may be any one or more of: the subject's intrinsic coherence; the intrinsic coherence of an individual having a disorder, a disease, a deficient mental characteristic, or any combination thereof; the intrinsic coherence of an individual not having the disorder, the disease, the deficient mental characteristic, or any combination thereof; the average intrinsic coherence of a population of individuals having a disorder, a disease, a deficient mental characteristic, or any combination thereof; and the average intrinsic coherence of a population of individuals not having the disorder, the disease, the deficient mental characteristic, or any combination thereof.

In some embodiments, the methods or devices described herein adjust the output of a Low Field Magnetic Stimulation device to generate a magnetic field for influencing an EEG phase between two sites in the brain of a subject of a specified EEG frequency toward a target EEG phase of the specified EEG frequency. The target EEG phase may be any one or more of: the subject's intrinsic EEG phase; the intrinsic EEG phase of an individual having a disorder, a disease, a deficient mental characteristic, or any combination thereof; the intrinsic EEG phase of an individual not having the disorder, the disease, the deficient mental characteristic, or any combination thereof; the average intrinsic EEG phase of a population of individuals having a disorder, a disease, a deficient mental characteristic, or any combination thereof; and the average intrinsic EEG phase of a population of individuals not having the disorder, the disease, the deficient mental characteristic, or any combination thereof.

Waveforms and Parameters of Magnetic Field

In some embodiments, the methods or devices described herein generate a magnetic field. The magnetic field can have any frequency, strength, gradient, position relative to the head of the subject, and the like suitable for influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

The strength of the magnetic field described herein is generally low. In some embodiments, the brain of the subject is stimulated to a level below the threshold for depolarization of the neurons in the brain of the subject.

In various embodiments, the magnetic field may have a strength of about 500 Gauss, about 400 Gauss, about 300 Gauss, about 200 Gauss, about 100 Gauss, about 75 Gauss, about 50 Gauss, about 40 Gauss, about 30 Gauss, about 25 Gauss, about 10 Gauss, about 5 Gauss, about 1 Gauss, or about 500 milli-gauss. In various embodiments, the magnetic field may have a strength of at most about 500 Gauss, at most about 400 Gauss, at most about 300 Gauss, at most about 200 Gauss, at most about 100 Gauss, at most about 75 Gauss, at most about 50 Gauss, at most about 40 Gauss, at most about 30 Gauss, at most about 25 Gauss, at most about 10 Gauss, at most about 5 Gauss, at most about 1 Gauss, or at most about 500 milli-gauss. In various embodiments, the magnetic field may have a strength of at least about 500 Gauss, at least about 400 Gauss, at least about 300 Gauss, at least about 200 Gauss, at least about 100 Gauss, at least about 75 Gauss, at least about 50 Gauss, at least about 40 Gauss, at least about 30 Gauss, at least about 25 Gauss, at least about 10 Gauss, at least about 5 Gauss, at least about 1 Gauss, or at least about 500 milli-gauss. In various embodiments, the magnetic field may have a strength of between about 50 Gauss and about 60 Gauss, between about 20 Gauss and about 100 Gauss, and the like. In various embodiments, the magnetic field may have a strength of at most about 9000 Gauss, at most about 8000 Gauss, at most about 7000 Gauss, at most about 6000 Gauss, at most about 5000 Gauss, at most about 4000 Gauss, at most about 3000 Gauss, at most about 2000 Gauss, at most about 1000 Gauss, at most about 900 Gauss, at most about 800 Gauss, at most about 700 Gauss, at most or about 600 Gauss. In various embodiments, the magnetic field may have a strength of between about 50 Gauss and about 60 Gauss, between about 20 Gauss and about 100 Gauss, and the like. In various embodiments, the magnetic field may have a strength of about 9000 Gauss, about 8000 Gauss, about 7000 Gauss, about 6000 Gauss, about 5000 Gauss, about 4000 Gauss, about 3000 Gauss, about 2000 Gauss, about 1000 Gauss, about 900 Gauss, about 800 Gauss, about 700 Gauss, or about 600 Gauss.

In some embodiments, the magnetic field is applied to a diffuse area of the brain, optionally the whole brain. This is in contrast to embodiments and methods wherein a specific area of the brain is targeted.

In some embodiments, the magnetic field is substantially uniform. The strength of the magnetic field can vary in any suitable way, but in some embodiments the magnetic field strength varies substantially linearly. In various embodiments the magnetic field has no gradient greater than about 1 Gauss/cm, greater than about 5 Gauss/cm, or greater than about 10 Gauss/cm. In some embodiments, the magnetic field is unidirectional.

The strength of the magnetic fields described herein generally change over time, generally in a periodic manner having a certain frequency. The magnetic field can vary according to any characteristic waveform ("shape") including those depicted in FIG. 3 such as a mono-phasic rectangular pulse 30, a bi-phasic rectangular pulse 31, a mono-phasic trapezoidal pulse 32, a bi-phasic trapezoidal pulse 33, a mono-phasic sinusoidal pulse 34, a bi-phasic sinusoidal pulse 35, a mono-phasic pulse train series 36, a bi-phasic pulse train series 37, or a sinusoid 38.

Frequency is the inverse of the interval of time in which the waveform repeats itself (period) and has units of Hertz (Hz; $s^{-1}$). The waveform and/or magnetic field can have any suitable frequency capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof.

In various embodiments the waveform and/or magnetic field has a frequency of about 1 Hz, about 2 Hz, about 3 Hz, about 4 Hz, about 5 Hz, about 6 Hz, about 7 Hz, about 8 Hz, about 9 Hz, about 10 Hz, about 11 Hz, about 12 Hz, about 13 Hz, about 14 Hz, about 15 Hz, about 16 Hz, about 17 Hz, about 18 Hz, about 19 Hz, about 20 Hz, about 22 Hz, about 24 Hz, about 26 Hz, about 28 Hz, about 30 Hz, about 50 Hz, about 100 Hz, about 150 Hz, and the like. In various embodiments the waveform and/or magnetic field has a frequency of at least about 1 Hz, at least about 2 Hz, at least about 3 Hz, at least about 4 Hz, at least about 5 Hz, at least about 6 Hz, at least about 7 Hz, at least about 8 Hz, at least about 9 Hz, at least about 10 Hz, at least about 11 Hz, at least about 12 Hz, at least about 13 Hz, at least about 14 Hz, at least about 15 Hz, at least about 16 Hz, at least about 17 Hz, at least about 18 Hz, at least about 19 Hz, at least about 20 Hz, at least about 22 Hz, at least about 24 Hz, at least about 26 Hz, at least about 28 Hz, at least about 30 Hz, at least about 50 Hz, at least about 100 Hz, at least about 150 Hz, and the like. In various embodiments the waveform and/or magnetic field has a frequency of at most about 1 Hz, at most about 2 Hz, at most about 3 Hz, at most about 4 Hz, at most about 5 Hz, at most about 6 Hz, at most about 7 Hz, at most about 8 Hz, at most about 9 Hz, at most about 10 Hz, at most about 11 Hz, at most about 12 Hz, at most about 13 Hz, at most about 14 Hz, at most about 15 Hz, at most about 16 Hz, at most about 17 Hz, at most about 18 Hz, at most about 19 Hz, at most about 20 Hz, at most about 22 Hz, at most about 24 Hz, at most about 26 Hz, at most about 28 Hz, at most about 30 Hz, at most about 50 Hz, at most about 100 Hz, at most about 150 Hz, and the like. In various embodiments the waveform and/or magnetic field has a frequency of between about 0.1 Hz and about 4 Hz, between about 4 Hz and about 8 Hz, between about 8 Hz and about 13 Hz, between about 13 Hz and about 30 Hz, between about 30 Hz and about 100 Hz, and the like.

Effects of Treatments

In some aspects, the devices or methods described herein improve at least one of: an indication in the subject; a disorder in the subject; a symptom in the subject; a dysfunction in the subject; a characteristic in the subject; and any combination thereof.

Since EEG changes can be direct consequences of treatments using the methods or devices described herein, in some embodiments, the EEG changes are used to clinically correlate improvement in the symptoms of a neurological disorder or improvement in cognitive performance. Improvement in symptoms can include positive symptoms and negative symptoms. In some embodiments, the EEG changes after using the methods or devices described correlated to both positive symptoms and negative symptoms. In some embodiments, the EEG changes after using the methods or devices described correlated to only positive symptoms. In some embodiments, the EEG changes after using the methods or devices described correlated to only negative symptoms. In some embodiments, correlations between EEG changes and improvement in negative symptoms are only significant in the absence of positive symptoms. In some embodiments, correlations between EEG changes and improvement in positive symptoms are only significant in the absence of negative symptoms.

In some embodiments, the indication is selected from the group consisting of replacement for meditation, quick nap, stress release, attention span, comprehension, memory, lowered blood pressure, increased libido, sports performance, academic performance, executive function, cognitive improvement, and any combination thereof.

In some embodiments, the disorder is selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof.

In some embodiments, the characteristic is selected from the group consisting of peripheral visual response, attention span, immediate reaction time (IRT), movement time (MT), simple perceptual reaction time (SPR), conflict perceptual reaction time (CPR), and any combination thereof.

In another aspect, the treatments described herein increase blood flow in the cortex of the subject. Since changes in blood flow and blood oxygenation in the brain are closely linked to neural activity, the treatments described herein may increase the neural activity of the cortex in some embodiments.

In some embodiments, the treatment improves at least one of neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, epilepsy, a movement disorder, a sleep disorder, a headache, lower back pain, neck pain, other generalized neuropathic pain, delirium, dementia, dizziness, vertigo, stupor, coma, a head injury, a stroke, multiple sclerosis, a demyelenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

In some embodiments, the subject is treated for major depression, depression, bipolar disorder, schizophrenia, anxiety disorder, obsessive-compulsive disorder, attention deficit hyperactivity disorder (ADHD), autism, autism spectrum disorders, sleep disorder, Parkinson's Disease, drug addiction, substance abuse, seizure, traumatic brain injury, Alzheimer's Disease, eating disorder, tinnitus, fibromyalgia, coma, post-traumatic stress disorder (PTSD), and any combination thereof.

In some embodiments, the treatment comprises improving cognitive function, executive function, academic performance, sports performance, peripheral visual response, attention span, immediate reaction time (IRT), movement time (MT), simple perceptual reaction time (SPR), conflict perceptual reaction time (CPR), or any combination thereof.

In some embodiments, methods and devices described herein can be used to improve at least two indications, disorders, symptoms, dysfunctions, characteristics, neuropathic pain, brain damage, cognitive function or any combination thereof from the group presented above. In some embodiments, methods and devices described herein can be used to improve at least three indications, disorders, symptoms, dysfunctions, characteristics, neuropathic pain, brain damage, cognitive function or any combination thereof from the group presented above. In some embodiments, methods and devices described herein can be used to improve at least four indications, disorders, symptoms, dysfunctions, characteristics, neuropathic pain, brain damage, cognitive function or any combination thereof from the group presented above.

PTSD

As used herein, "posttraumatic stress disorder" or "post-traumatic stress disorder" or "PTSD" means a neurological disorder that develops after exposure to a traumatic event. The diagnostic criteria for PTSD are: (a) exposure to a traumatic event (i.e.; the person experienced, witnessed, or was confronted with an event or events that involved actual or threatened death or serious injury, or a threat to the physical integrity of self or others; and the person's response involved intense fear, helplessness, or horror); (b) persistent re-experience of the traumatic event; (c) persistent avoidance of stimuli associated with the trauma; (d) persistent symptoms of increased arousal (e.g. difficulty falling or staying asleep, anger and hypervigilance); (e) significant impairment in social or occupational functioning; and (f) duration of symptoms is for more than 1 month.

In some embodiments, the brain waves of a subject suffering from PTSD are primarily characterized by periods of complex and chaotic firing (i.e. low Q-factor), and occasional periods of more rhythmic firing (i.e., high Q-factor). In some embodiments, adjusting the brain waves of a subject with PTSD to increase the rhythmic-ness of the waves results (partially or fully) in a decrease in the symptoms of PTSD.

Coma

As used herein, "coma" means a neurological disorder characterized by a profound state of unconsciousness. Subjects in a comatose state (i.e., in a coma) do not have sleep-wake cycles, cannot be awakened, fail to respond to stimuli (e.g., pain or light), and do not take voluntary actions. In certain instances, a subject will emerge from a coma in varying levels of consciousness (e.g., vegetative to fully conscious). In some embodiments, stimulating the area of the brain responsible for arousal results (partially or fully) in a subject emerging from a coma. In some embodiments, a subject in a coma displays slow sinusoidal brain waves. In some embodiments, stimulating a subject's brain waves at their alpha frequency results in the subject emerging from a coma. In some embodiments, stimulating a subject's brain waves at or near their alpha frequency results in the subject emerging from a coma. In some embodiments, stimulating a subject's brain waves at 9.6 Hz results in the subject emerging from a coma. In some embodiments, as the subject regains consciousness, the frequency used to stimulate the subject's brain waves is adjusted. In some embodiments, as the subject regains consciousness, the frequency used to stimulate the subject's brain waves is adjusted to a frequency closer to their alpha frequency.

Amblyopia

As used herein, "amblyopia" is a neurological disorder characterized by poor or indistinct vision in a physiologically normal eye. In certain instances, the disorder results from no transmission or poor transmission of visual images to the brain for a sustained period of time. In some embodiments, subjects with amblyopia display asymmetric activity in the occipital lobe. In some embodiments, increasing the symmetry of activity in the occipital lobe decreases the symptoms of amblyopia. In some embodiments, applying a magnetic field at the alpha frequency across the whole brain improves the coherence. In some embodiments, increasing coherence lessens the effects of the amblyopia.

Parkinson's Disease

As used herein, "Parkinson's disease" means a degenerative neurological disorder characterized by a progressive loss of motor control. In some embodiments, Parkinson's disease results from a deficiency in dopamine levels. In certain instances, deficient dopamine levels results in the increased and uncontrolled firing of neurons. In certain instances, the cells of the substantia nigra generate dopamine. In certain instances, loss of cells in the substantia nigra (and the resulting dopamine deficiency) results in (partially or fully) the development of Parkinson's.

A common symptom of Parkinson's is the rhythmic tremor. In some embodiments, the rhythmic tremor results from neurons firing at a frequency of 4-5 Hz. In some embodiments, adjusting the brain waves of a subject with Parkinson's results (partially or fully) in a decrease in rhythmic tremors. In some embodiments, applying a magnetic field at a frequency greater than the frequency of a rhythmic tremor (i.e., 4-5 Hz) accentuates the EEG frequency equal to that of the alternating magnetic field. In some embodiments, adjusting the magnetic field decreases the influence of the EEG frequency that causes the tremors. In some embodiments, shifting the subject's alpha frequency higher or lower reduces the tremors. In some embodiments, shifting the subject's alpha frequency results in the alpha frequency no longer a $2^{nd}$ harmonic of the patient's tremor frequency. Disclosed herein, in certain embodiments, are methods of treating Parkinson's disease. As used herein, "treating Parkinson's disease" means an improvement as measured using the Unified Parkinson's Rating Scale. The modified Unified Parkinson's Rating Scale may include, for non-limiting example, measuring muscle tone and knee/arm flexibility.

Cognitive Performance Improvement

In certain instances, cognitive performance is affected by neural firing patterns. In some embodiments, a subject displaying rhythmic neural firing patterns processes complex information quicker and more accurately than a subject with more chaotic (i.e., less rhythmic) neural firing patterns. In some embodiments, increasing the rhythmic-ness of brain waves results (partially or fully) in (a) an increase in the rate at which the subject learns, (b) an increase in the speed at which the subject reacts to stimuli, (c) an increase in attentiveness, (d) an increase in the ability of the subject to concentrate, or a combination thereof. In some embodiments, the brain of a subject under pressure and/or stress deviates from its natural energy to a higher energy. In some embodiments, the brain of a subject under pressure and/or stress deviates from its natural rhythmic state to a more un-rhythmic state.

In some embodiments, the subject's average alpha frequency is measured. In some embodiments, the frequency of the applied magnetic field is set to the value of the subject's average alpha frequency. In some embodiments, applying the magnetic field at a value equal to the subject's average alpha frequency brings the brain back to its natural state, which is optimal for concentration, focus, and performance in a variety of tasks. Disclosed herein, in certain embodiments, are methods of improving cognitive performance. As used herein, "cognitive performance" means the rate at which a subject processes information. Cognitive performance includes, but is not limited to, (a) the rate at which a subject learns, (b) the speed at which a subject reacts to stimuli, (c) a subject's attentiveness, (d) a subject's ability to concentrate, or a combination thereof. In some embodiments, improving cognitive performance improves military performance (e.g., the performance of a solider under battlefield conditions). In some embodiments, improving cognitive performance improves athletic performance (e.g., the ability of an athlete to react to stimuli). In some embodiments, improving cognitive performance improves academic performance (e.g., the ability to perform on standardized tests).

Major Depressive Disorder

Major Depressive Disorder (MDD) is an illness that is generally marked by a range of emotional as well as physical symptoms, including depressed mood, loss of energy, sleep disturbance, and cognitive deficits. In some embodiments, these symptoms appear to be related to disturbances in brain function in MDD, which in turn are related to the severity of the symptoms of the illness. These disturbances may include (a) decreased cerebral blood flow and metabolism and/or (b) dysregulation of cerebral oscillatory activity.

In some embodiments, MDD is marked by increased alpha frequency (8-12 Hz) band synchrony particularly over the frontal brain regions, and a putative mechanism of action (MOA) of the treatments described herein is restoration of normal alpha band oscillatory activity. Described herein is a physical model that characterizes alpha band synchrony, both prior to treatment and after administration of treatment which may be more accurate than traditional quantitative electroencephalographic (qEEG) power measures. Based upon this model, delivery of treatment through continuous sinusoidal stimulation at a subject's average IAF, rather than intermittent pulsatile stimulation at a fixed 10 Hz setting, may be more effectively at restoring normal cortical oscillatory activity. This method of administering sinusoidal waveforms at a subject's average individual alpha frequency (IAF) may theoretically provide a greater likelihood of entraining cortical oscillations and may be more consistent with the emerging understanding of the MOA of the therapies described herein. Treatments delivered broadly with low magnetic field intensity may be the treatment approach that is most consistent with the EEG and cerebral blood flow abnormalities generally distributed throughout the frontal regions in MDD. Described herein is a system for this mode of stimulus delivery to reset the amplitude and synchronization of the EEG rhythms, and thereby improving the symptoms of MDD.

CERTAIN DEFINITIONS

Unless otherwise defined, all technical and scientific terms used herein have the same meaning as commonly understood by one of ordinary skill in the art to which this invention belongs.

As used in this specification and the appended claims, the singular forms "a," "an," and "the" include plural references unless the context clearly dictates otherwise. Thus, for example, references to "a subject" includes one or more subjects described herein which will become apparent to those persons skilled in the art upon reading this disclosure and so forth. Any reference to "or" herein is intended to encompass "and/or" unless otherwise stated.

As used in this specification and the appended claims, the term "about" means that the stated parameter can vary by as much as 0.1%, as much as 1%, as much as 5%, as much as 10%, as much as 20%, as much as 50% in various embodiments.

As used herein, "subject" means a mammal, preferably a human mammal. The term "subject" does not require the oversight (either continuous or intermittent) of a medical or scientific professional (e.g., a physician, nurse, physician's assistant, clinical research associate, orderly, and hospice worker); however, the term does not preclude the oversight of a medical or scientific professional.

As used herein, a "control group" means a set of subjects having a particular trait, characteristic, ability, or feature (e.g., a certain level of cognitive performance); or a set of subjects not having a neurological disorder mentioned herein. In some embodiments, the control group comprises at least two subjects.

As used herein, "alpha frequency" means a type of brain wave predominantly found to originate from the occipital lobe during periods of waking relaxation. In certain instances, alpha waves are attenuated during periods of sleep.

As used herein, "waveform" means the shape and form of a signal such as a wave moving in a physical medium or an abstract representation. In some cases, the term "waveform" refers to the shape of a graph of the varying quantity against time or distance.

The various functions or processes disclosed herein (such as, for non-limiting example, logic that performs a function or process) may be described as data and/or instructions embodied in various computer-readable media, in terms of their behavioral, register transfer, logic component, transistor, layout geometries, and/or other characteristics. The logic described herein may comprise, according to various embodiments of the invention, software, hardware, or a combination of software and hardware. The logic described herein may comprise computer-readable media, Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of components and/or processes under the ICS may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

The elements and acts of the various embodiments described can be combined to provide further embodiments. These and other changes can be made to the system in light of the above detailed description.

In general, in the following claims, the terms used should not be construed to limit the system, methods, or devices to the specific embodiments disclosed in the specification and the claims, but should be construed to include all processing systems that operate under the claims. Accordingly, the system, methods, and devices are not limited by the disclosure, but instead the scopes of the system, methods, or devices are to be determined entirely by the claims.

While certain aspects of the system, methods, or devices are presented below in certain claim forms, the inventors contemplate the various aspects of the system, methods, or devices in any number of claim forms. For example, while only one aspect of the system, methods, or devices is recited as embodied in machine-readable medium, other aspects may likewise be embodied in machine-readable medium. Accordingly, the inventors reserve the right to add additional claims after filing the application to pursue such additional claim forms for other aspects of the system, methods, or devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The invention is described in greater detail by the following non-limiting examples.

Example 1

Characterization of the Effect of Therapy on Cerebral Oscillatory Activity

In order to illustrate a possible physical model that adequately characterizes synchronization, consider the qEEG power spectrum of a subject with moderate alpha band synchrony.

Figure 9:
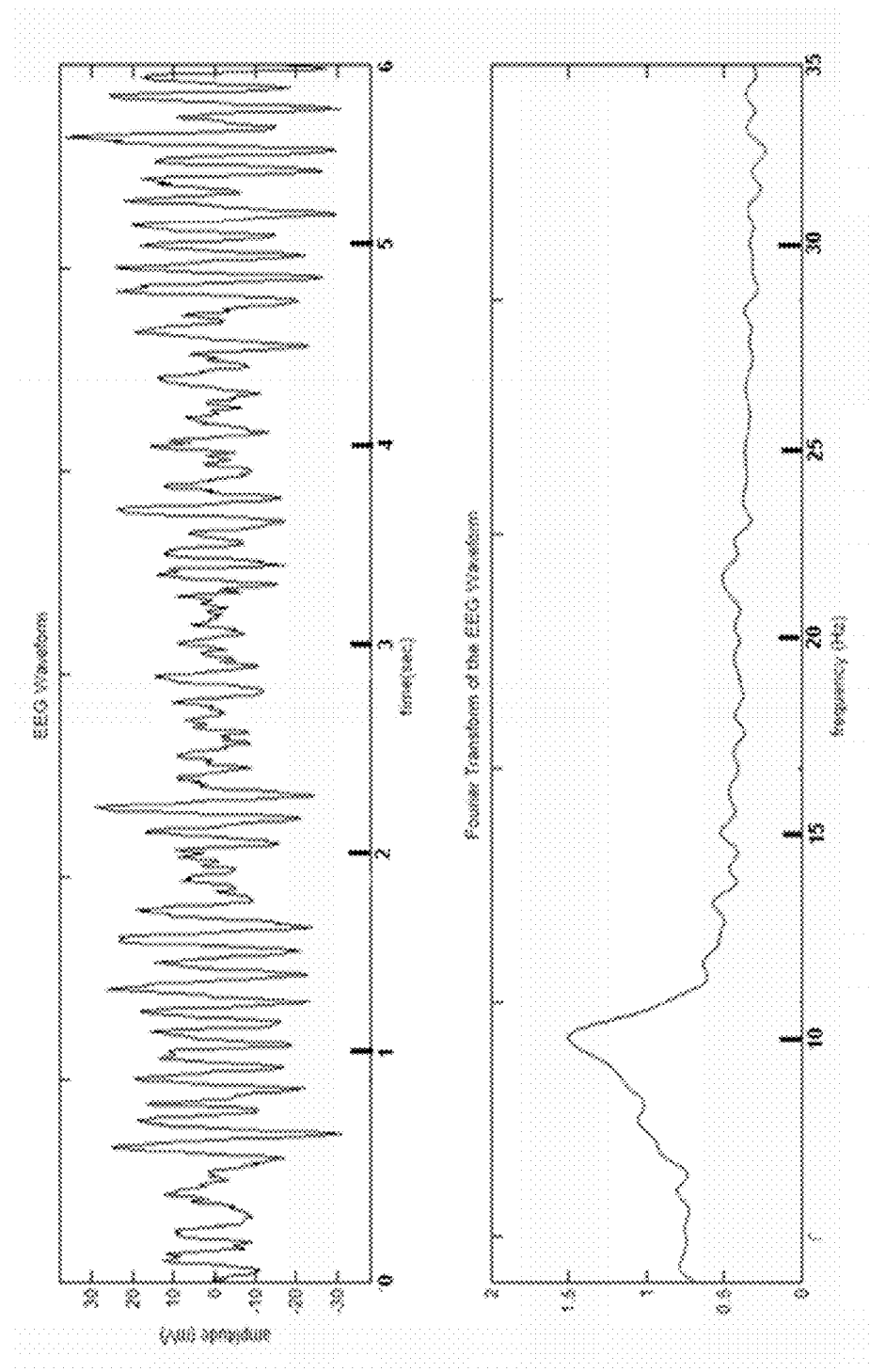
FIG. 9 depicts an EEG in time domain (above) and the associated power spectrum in the frequency domain (below) of a recording of moderately synchronous alpha activity.

FIG. 9 shows the EEG signal in the time domain (top panel) and the associated power spectrum in the frequency domain (bottom panel). The top panel is the EEG waveform. The vertical axis of the top panel is amplitude measured in mV ranging from −40 mV at the bottom to 40 mV at the top, centered at zero mV. The horizontal axis of the top panel is time measured in seconds ranging from zero at the left to 6 seconds at the right. The bottom panel is the Fourier transform of the EEG waveform depicted in the top panel. The vertical axis is the energy in the signal and ranges from zero at the bottom to two at the top. The horizontal axis is frequency measured in Hz ranging from zero at the left to 35 Hz at the right. The power spectrum shows a peak at approximately 10 Hz, with power broadly distributed at higher and most notably lower frequencies. The EEG depicted in FIG. 9 has moderately synchronous alpha activity.

Figure 10:
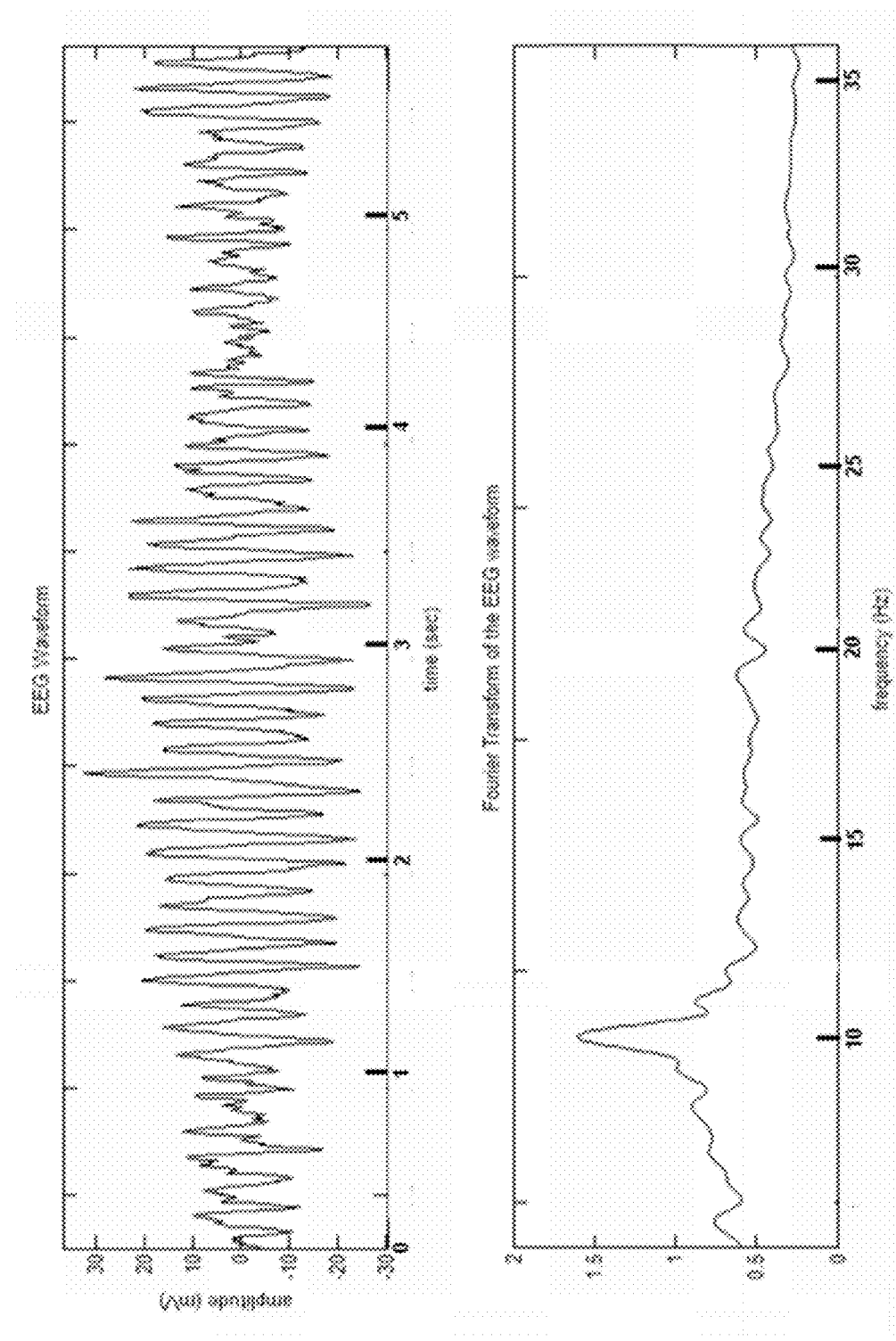
FIG. 10 depicts an EEG in time domain (above) and the associated power spectrum in the frequency domain (below) of a recording of high synchronous alpha activity.

FIG. 10 shows the EEG and power spectrum for a subject with more synchronous alpha activity. The top panel is the EEG waveform. The vertical axis of the top panel is amplitude measured in mV ranging from −30 mV at the bottom to 40 mV at the top, centered at zero mV. The horizontal axis of the top panel is time measured in seconds ranging from zero at the left to 6 seconds at the right. The bottom panel is the Fourier transform of the EEG waveform depicted in the top panel. The vertical axis is the energy in the signal and ranges from zero at the bottom to two at the top. The horizontal axis is frequency measured in Hz ranging from zero at the left to just more than 35 Hz at the right. The more synchronous tracing results in a narrower spectral peak within the alpha frequency band. The alpha band energy commonly is characterized through measurement of absolute power (the intensity of the energy in microvolts squared) as well as relative power (the proportion of the total energy of the signal that is present in the alpha band). These two recordings have comparable absolute and relative power, demonstrating how these metrics describe only incompletely the energy output of the cortex. There can be marked differences in synchrony within the alpha band without a significant change in total power.

The degree of synchronization within the band is more completely characterized by Q factor analysis of the power spectrum. The Q factor represents the ratio of the total energy contained in a system divided by the energy lost in a single oscillation of the system. It can be characterized by the equation $$Q = \frac{f_0}{\Delta f}$$

in which $f_0$ is the patient's average individual alpha frequency (IAF) and $\Delta f$ is the bandwidth at a 3 db drop from the IAF peak (i.e., the width between the boundaries for the range of frequencies where the system energy is at half its peak value) (FIG. 4). The Q factor provides a quantitative representation of the synchrony of an oscillatory system in a given frequency band. If the system has a high Q at the IAF, then it has a higher concentration of synchronized energy output in the alpha band and therefore a "purer" or more synchronized signal.

Figure 11:
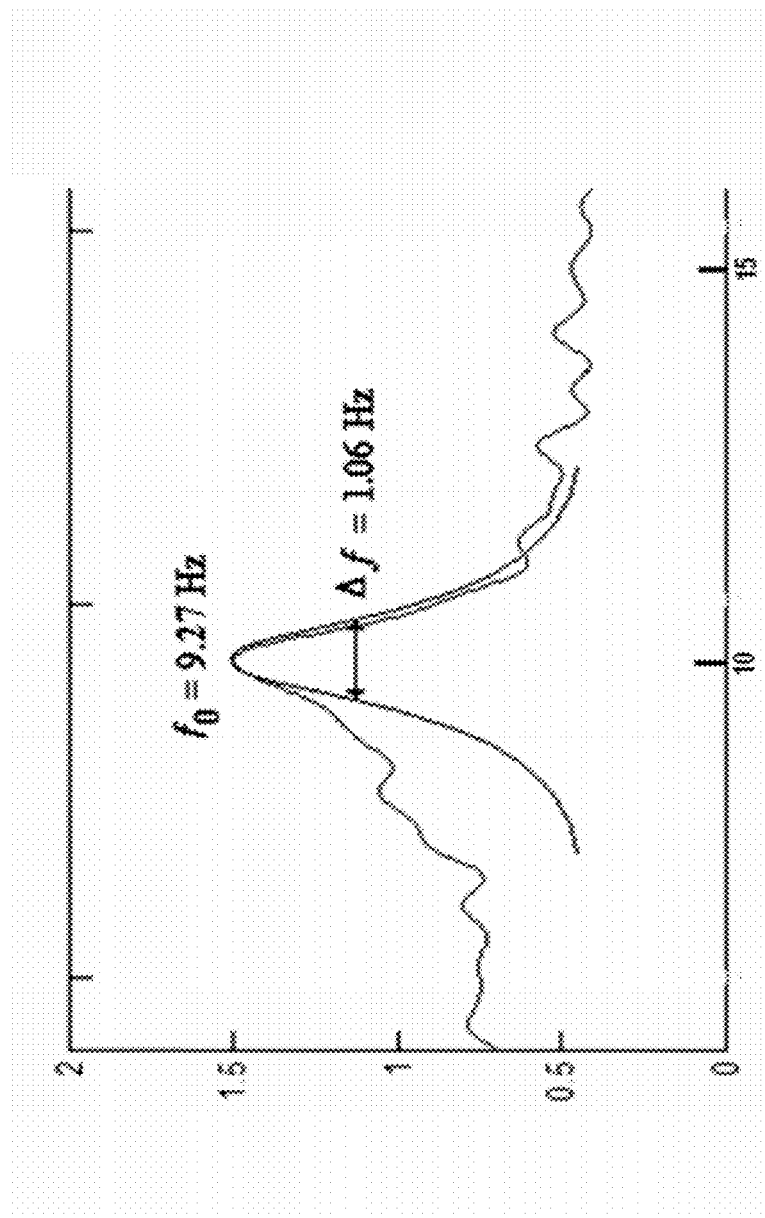
FIG. 11 depicts the power spectrum from FIG. 9 with a fitted Gaussian waveform to illustrate the Q factor.

The Q factor of the EEG waveform can be approximated for an individual EEG segment by fitting a Gaussian-shaped curve to the frequency spectrum of that segment. FIG. 11 is a Fourier transform that depicts the power spectrum from FIG. 9 with a fitted Gaussian waveform to illustrate the Q factor. The vertical axis is the energy in the signal ranging from zero at the bottom to two at the top. The horizontal axis is frequency measured in Hz and ranges from zero to 15 Hz at the right. Here, $f_0$ is 9.27 Hz and $\Delta f$ is 1.06 Hz. In this case, the Q factor is 8.74.

Figure 12:
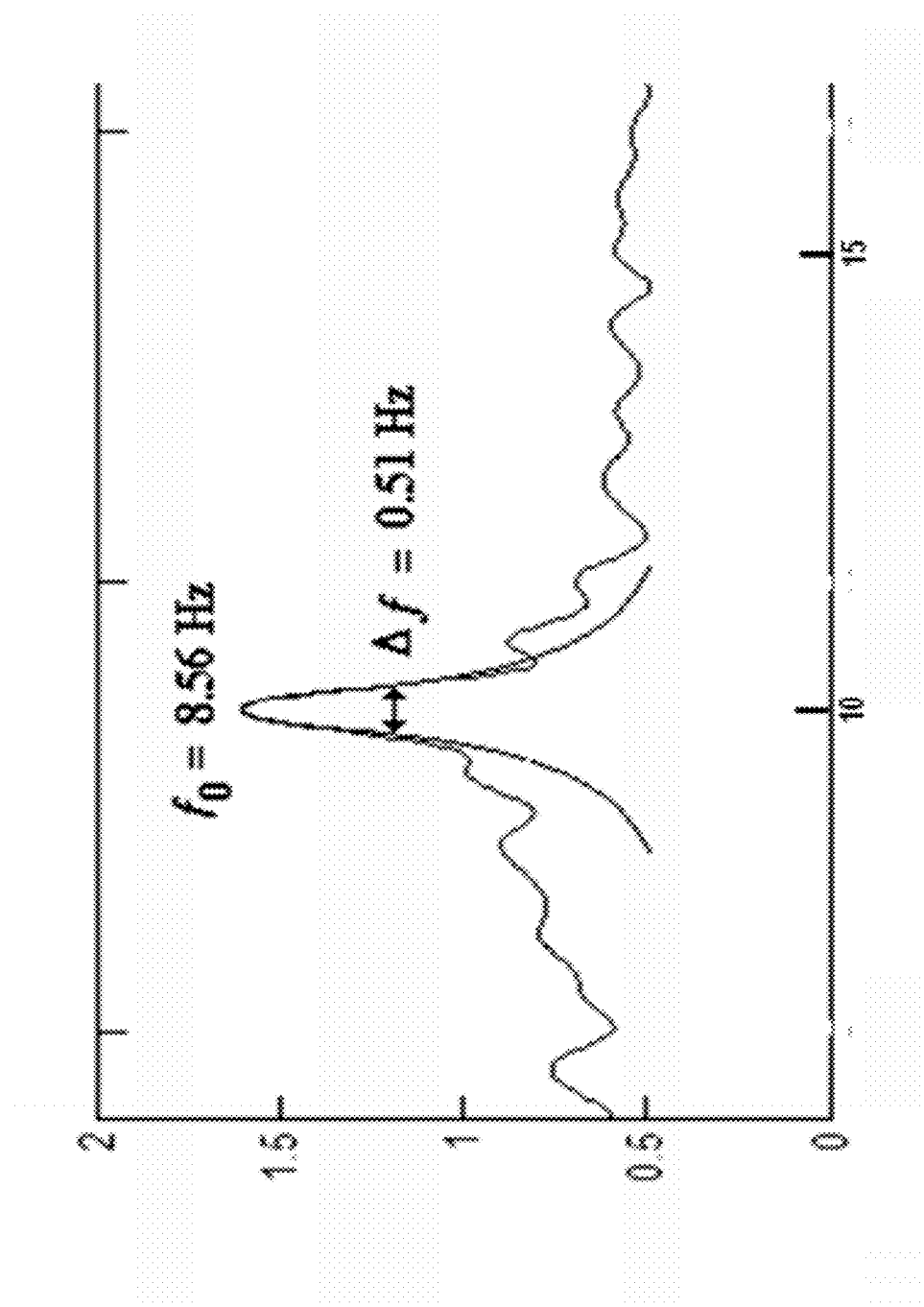
FIG. 12 depicts the power spectrum from FIG. 10 with a fitted Gaussian waveform to illustrate the Q factor.

FIG. 12 is a Fourier transform that depicts the power spectrum from FIG. 10 with a fitted Gaussian waveform to illustrate the Q factor. The vertical axis is the energy in the signal ranging from zero at the bottom to two at the top. The horizontal axis is frequency measured in Hz and ranges from zero to 15 Hz at the right. Here, $f_0$ is 8.56 Hz and $\Delta f$ is 0.51 Hz. In this case, the Q factor is 16.78.

Example 2

Sinusoidal Magnetic Stimulation Synchronized to the Average IAF

Figure 13:
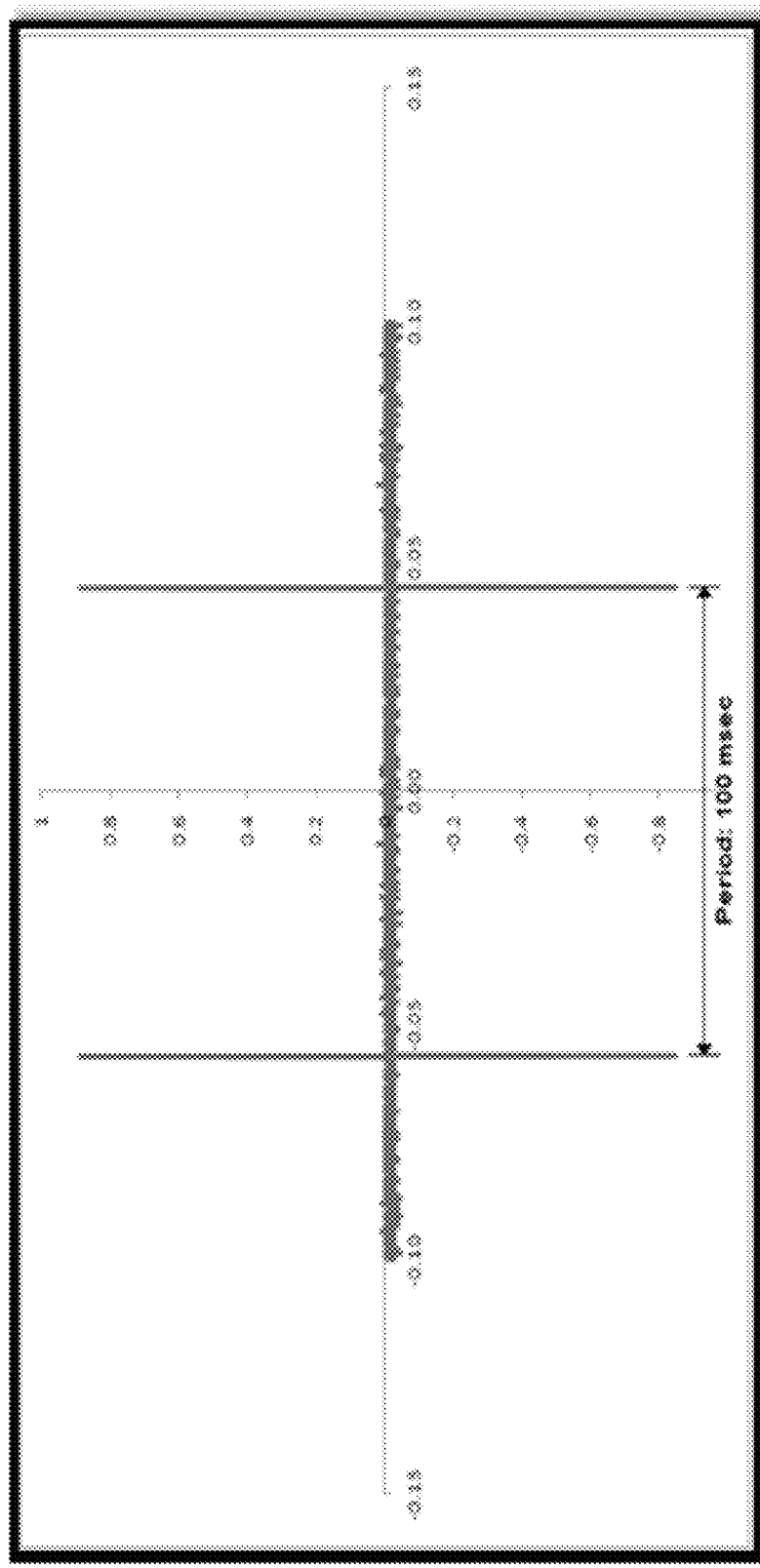
FIG. 13 depicts a pulse waveform with a period of 10 pulses/sec.

In some instances, a focal pulsatile stimulation waveform over the left dorsolateral prefrontal cortex at a frequency of 10 Hz commonly is used in treatment of MDD. However, pulsed fields do not consist of a pure 10 Hz signal. An example of a pulse is shown in FIG. 13. The vertical axis is the field strength measured in Tesla ranging from −1 Tesla at the bottom to 1 Tesla at the top, centered at zero. The horizontal axis is time ranging from −0.15 seconds at the left to 0.15 seconds at the right, centered at zero. The pulse has a period of 100 milli-seconds or ten pulses per second.

Figure 14:
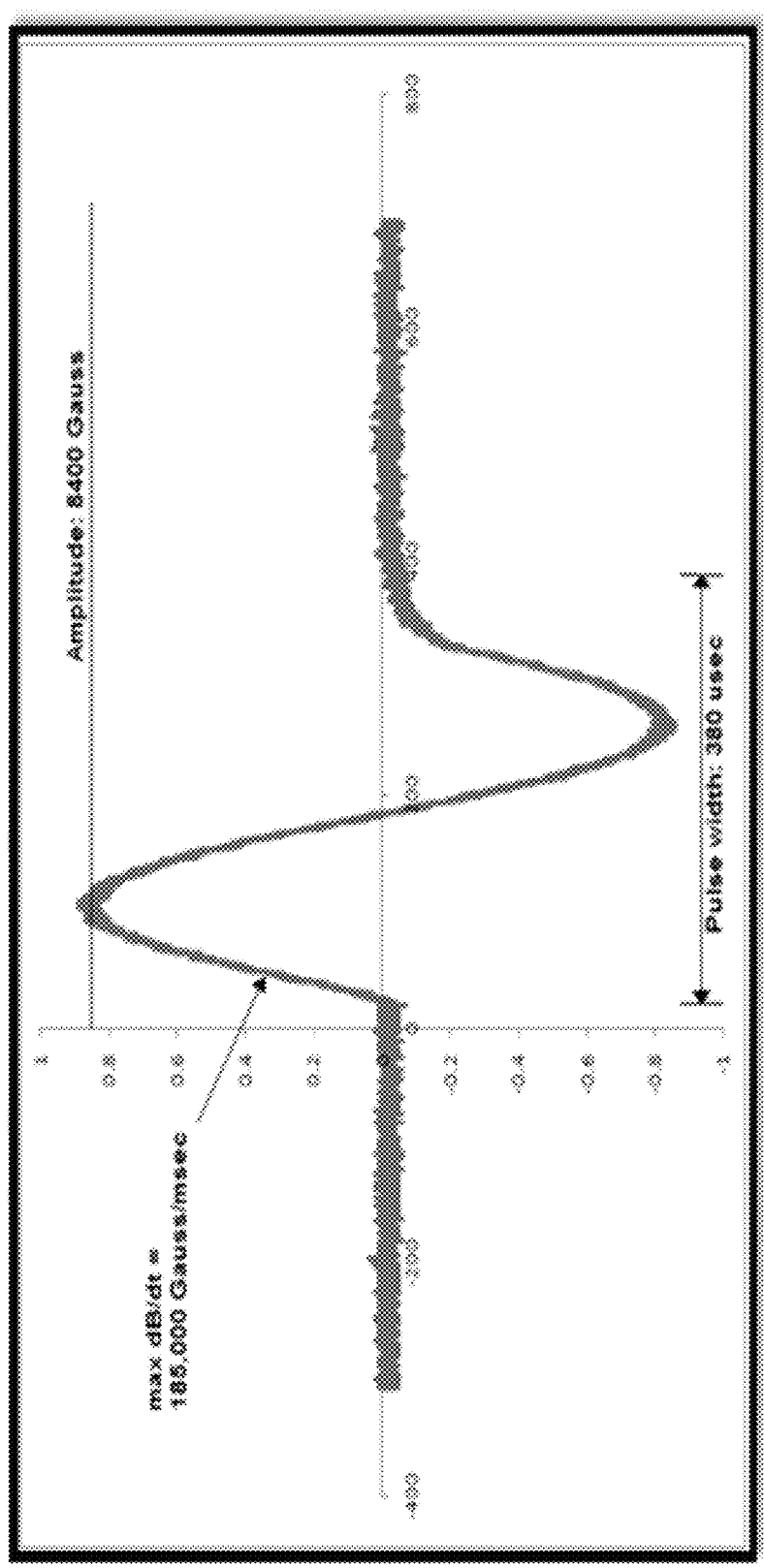
FIG. 14 depicts the waveform of a single pulse on an expanded time scale.

FIG. 14 depicts the waveform of a single pulse of FIG. 13 on an expanded time scale. The expanded time scale shows that the pulse comprises a single sinusoidal period. In FIG. 14, the vertical axis is the field strength measured in Tesla ranging from −1 Tesla at the bottom to 1 Tesla at the top, centered at zero. The waveform has an amplitude of about 8,400 Gauss. The horizontal axis is time ranging from −400 micro-seconds at the left to 800 micro-seconds at the right. The pulse has a width of about 380 micro-seconds. The maximum rate of change in the field strength is about 185,000 Gauss/msec.

Figure 15:
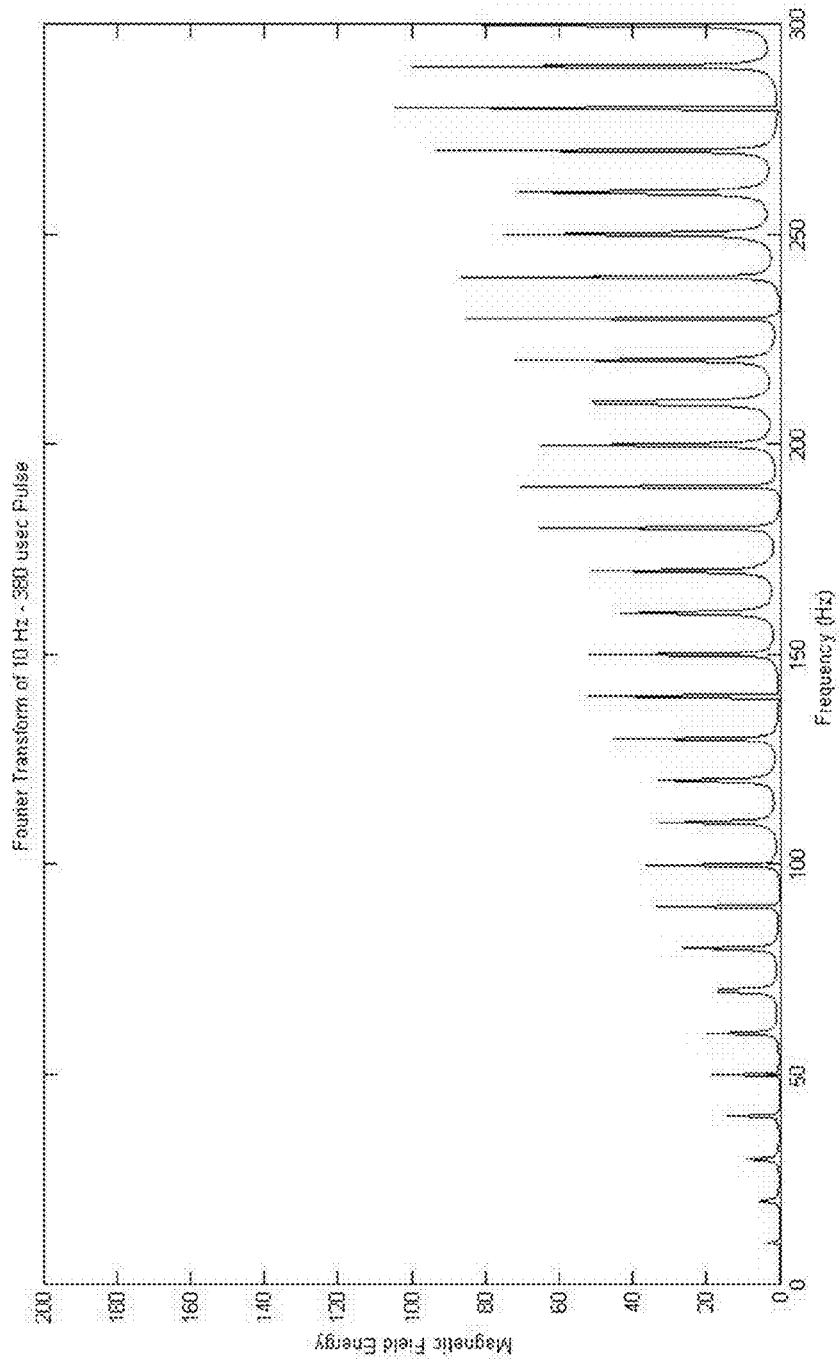
FIG. 15 depicts the Fourier transform of a pulse at 10 Hz.

Shown on an expanded time scale, the pulse is shown to consist of a more complex waveform (FIG. 14) whose Fourier series has energy being transmitted at a broad range of harmonic frequencies (FIG. 15). These higher-order harmonics in the pulse may help to explain why the EEG response to pulsed waveforms commonly often contain "noise" at multiple higher frequencies (e.g., 20 Hz, 30 Hz). FIG. 15 is the Fourier transform of a pulse at 10 Hz. The vertical axis is magnetic field energy and ranges from zero at the bottom to 200 at the top. The horizontal axis is frequency measured in Hz and ranges from zero at the left to 300 at the right.

In the example described herein, given the putative MOA of MDD treatment of modulation of cortical oscillations at the IAF, a sinusoidal waveform is delivered at the IAF. This example may be at least as effective, and possibly more effective, at resetting local cortical oscillators and achieving therapeutic benefit than a pulsed waveform. If the brain is modeled as a resonant system with the IAF as its intrinsic frequency, then in order to affect the system, imparting energy at or near the IAF would be expected to have the greatest effect on the oscillations. A sinusoidal magnetic field is much more "targeted" from a frequency perspective, and therefore may have a greater effect on resetting the oscillatory system in the brain than traditional pulses.

Figure 16:
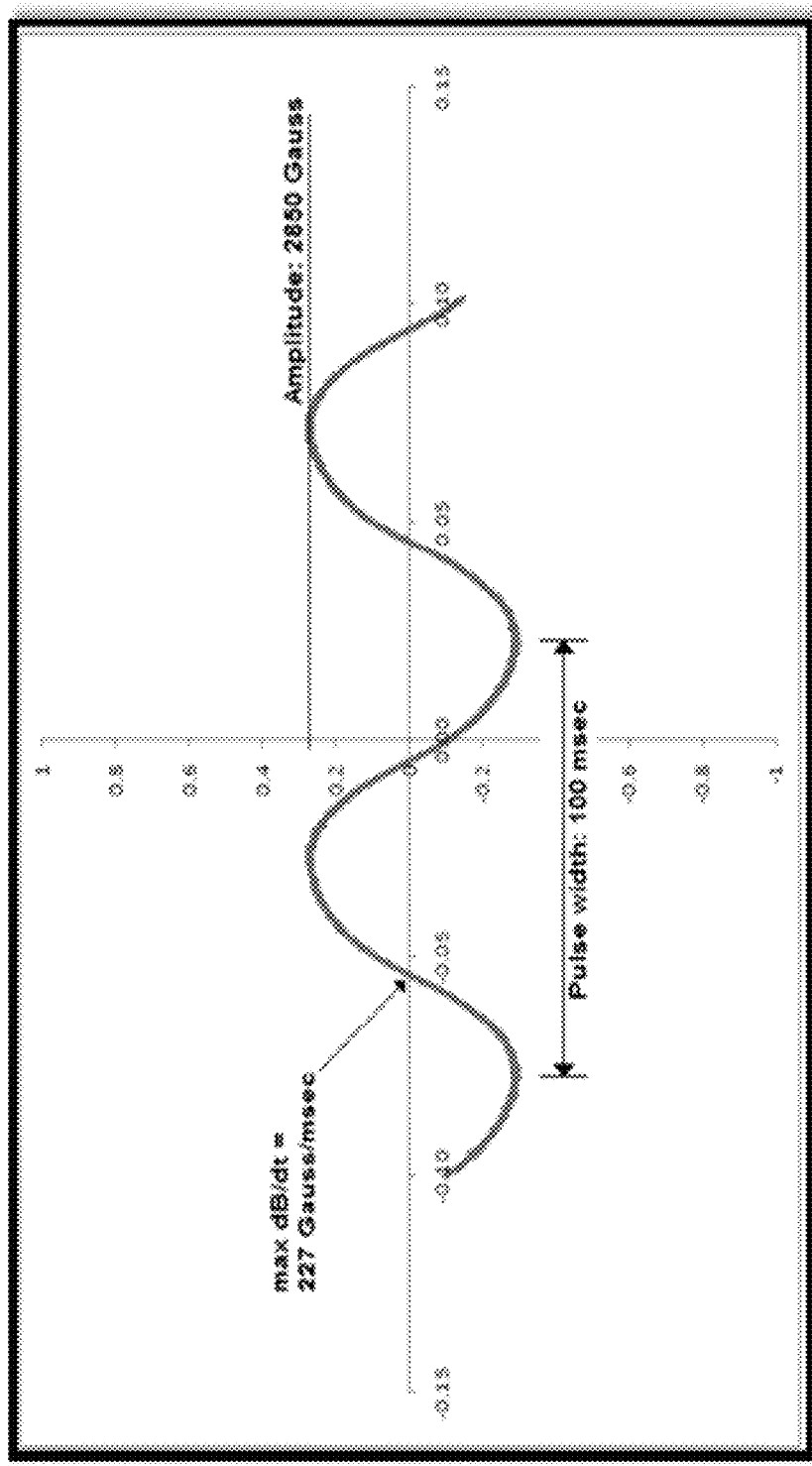
FIG. 16 depicts a sinusoidal waveform at a sample IAF of 10 Hz.

For example, FIG. 16 depicts a sinusoidal waveform at a sample IAF of 10 Hz. The vertical axis is field strength measured in Tesla and ranges from −1 Tesla at the bottom to 1 Tesla at the top, centered at zero. The horizontal axis is time measured in seconds ranging from −0.15 seconds at the left to 0.15 seconds at the right, centered at zero. The sinusoidal waveform has a pulse width of 100 milli-seconds and an amplitude of 2850 Gauss. The maximum rate of change in amplitude is about 227 Gauss/msec.

Figure 17:
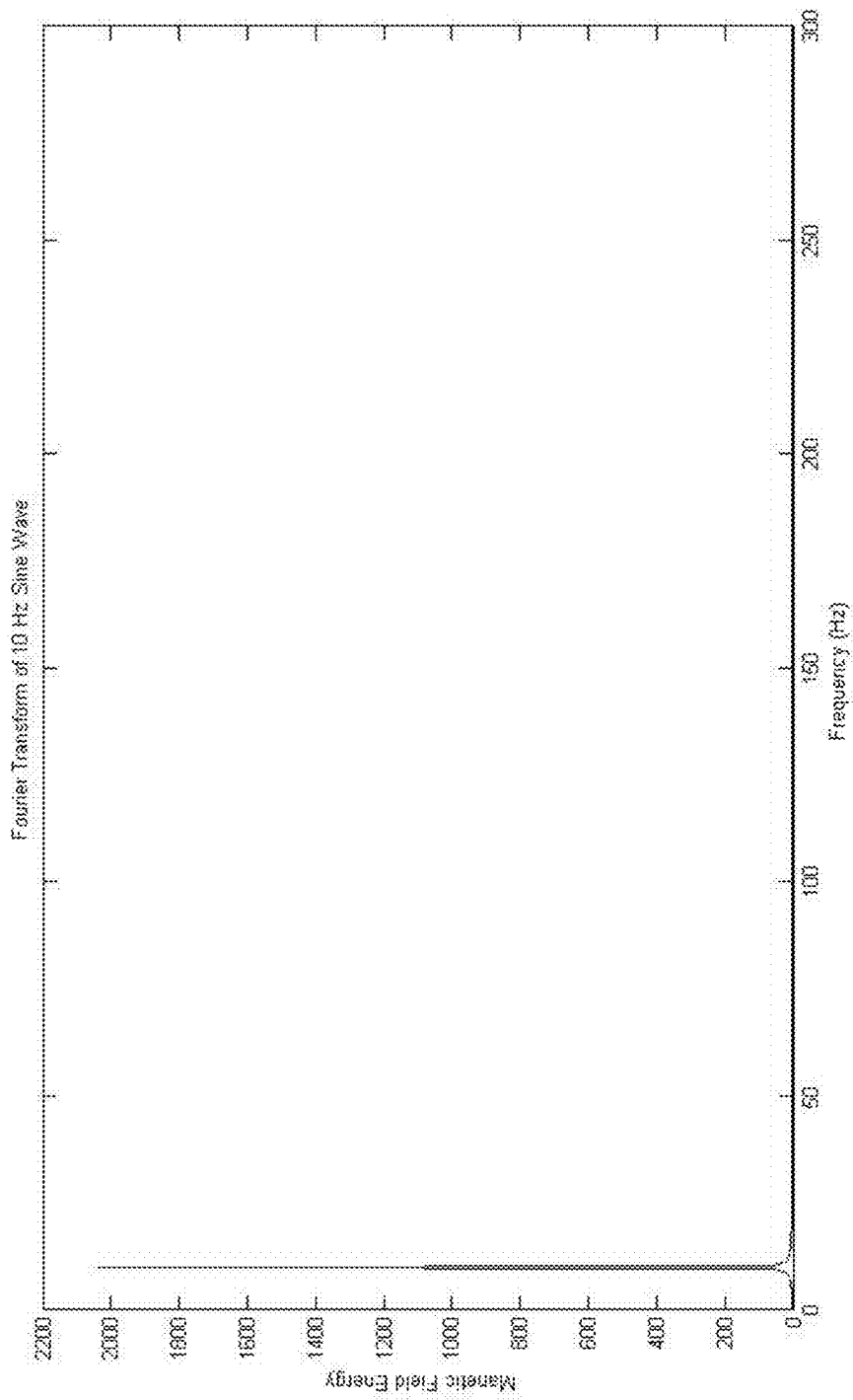
FIG. 17 depicts a Fourier transform of a sinusoidal stimulus waveform with a frequency of 10 Hz.

FIG. 17 depicts a Fourier transform of a sinusoidal stimulus waveform with a frequency of 10 Hz, such as the waveform depicted in FIG. 16. FIG. 17 is entitled "Fourier Transform of 10 Hz Sine Wave". The vertical axis is the Magnetic Field Energy and ranges from zero at the bottom to 2200 at the top. The horizontal axis is frequency measured in Hz and ranges from zero at the left to about 300 at the right.

A sinusoidal waveform (FIG. 16) more closely mimics the natural oscillations of the cerebral cortex and yields a "pure" power spectrum at the intended average IAF (FIG. 17).

What is claimed is:

1. A Low Field Magnetic Stimulation device comprising:
   a. a user interface comprising a control;
   b. a waveform generator in communication with the user interface;
   c. at least one coil;
   d. a magnetic field generated by a direct conversion by the coil of an electrical waveform generated by the waveform generator; and
   e. non-transitory computer-readable media encoded with a software module including a command executable by a processor that receives an input at the user interface, the input comprising:
   an intrinsic frequency of the subject within an EEG band, or a Q-factor of the intrinsic frequency of the subject within the EEG band; and
   a first direction of moving the intrinsic frequency of the subject up or down within the EEG band, or a second direction of moving the Q-factor of the intrinsic frequency of the subject up or down within the EEG band, and adjusts the electrical waveform and thereby the magnetic field based on the input, the adjustment comprising:
   generating, in the magnetic field, a first frequency in an EEG band that is higher than an intrinsic frequency in the EEG band of the subject, when the first direction is up;
   generating, in the magnetic field, a second frequency in the EEG band that is lower than the intrinsic frequency in the EEG band of the subject, when the first direction is down;
   generating, in the magnetic field, a first target frequency in the EEG band of the subject, when the second direction is up;
   generating, in the magnetic field, a second target frequency in the EEG band of the subject, when the second direction is down; or
   generating, in the magnetic field, a plurality of frequencies, when the second direction is down, wherein each of the plurality of frequencies is within a pre-determined frequency range,
   wherein at least one of (a) a strength of the magnetic field is more than 0 Gauss and less than about 100 Gauss, (b) the magnetic field is uniform, (c) the magnetic field is configured to target the whole brain, and (d) the waveform has a frequency of at least about 1 Hz and less than about 100 Hz,
   wherein the magnetic field is applied close to a head of the subject, and
   wherein the Q-factor of the intrinsic frequency is the intrinsic frequency within the EEG band divided by a frequency bandwidth comprising frequencies that are within the EEG band and having energy at or above half of the energy at the intrinsic frequency within the EEG band.

2. The device of claim 1, wherein the magnetic field is generated by a coil configured to encircle the head of the subject, wherein the magnetic field is generated by a plurality of coils around the head of the subject, or wherein the magnetic field is generated by a coil that can be positioned over a region of interest on the head of the subject.

3. The device of claim 1, wherein the device is configured to stimulate a brain of the subject to a level below the threshold for depolarization of the neurons in the brain of the subject.

4. The device of claim 1, wherein the magnetic field is uniform, wherein the magnetic field strength varies linearly, wherein the magnetic field has a gradient greater than about 5 Gauss/cm, and/or wherein the magnetic field is unidirectional.

5. The device of claim 1, wherein the magnetic field varies according to a waveform, wherein the waveform is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid.

6. The device of claim 1, wherein the waveform has a period of less than about 10 msec, wherein the waveform has a frequency between about 8 Hz and about 13 Hz, wherein the strength of the magnetic field is less than about 100 Gauss and no less than 1.5 Gauss.

7. The device of claim 1, wherein the first target frequency is the intrinsic alpha frequency (IAF) of the subject.

8. A method for treating a subject comprising:
   operating a magnetic field generator that is configured to generate a magnetic field, wherein a strength of the magnetic field is more than 0 Gauss and less than about 100 Gauss;
   adjusting the magnetic field of the magnetic field generator based on an intrinsic frequency of the subject within an EEG band or a Q-factor of the intrinsic frequency of the subject within the EEG band as follows:
   moving the intrinsic frequency of the subject up within an EEG band by generating a first frequency in the EEG band that is higher than the intrinsic frequency in the EEG band of the subject;

moving the intrinsic frequency of the subject down within the EEG band by generating a second frequency in the EEG band that is lower than the intrinsic frequency in the EEG band of the subject;

moving a Q-factor of the intrinsic frequency up by generating a first target frequency in the EEG band of the subject;

moving the Q-factor of the intrinsic frequency down by generating a second target frequency in the EEG band; or moving the Q-factor of the intrinsic frequency down by generating a plurality of frequencies, wherein each of the plurality of frequencies is within a pre-determined frequency range, and applying the magnetic field close to a head of the subject, wherein the Q-factor of the intrinsic frequency is the intrinsic frequency within the EEG band divided by a frequency bandwidth comprising frequencies that are within the EEG band and having energy at or above half of the energy at the intrinsic frequency within the EEG band.

9. The method of claim 8, wherein the subject is treated for about 1 minute to about 1 hour, and wherein the treatment is repeated after an interval of about 6 hours to about 14 days.

10. The method of claim 8, wherein the magnetic field generated is below the threshold for depolarization of the neurons in the brain of the subject.

11. The method of claim 8, wherein the magnetic field is uniform, wherein the magnetic field strength varies linearly, wherein the magnetic field has a gradient greater than about 5 Gauss/cm, wherein the magnetic field is unidirectional.

12. The method of claim 8, wherein the magnetic field is applied to a diffuse area of the brain of the subject.

13. The method of claim 8, wherein the magnetic field varies according to a waveform that is a mono-phasic rectangular pulse, a bi-phasic rectangular pulse, a mono-phasic trapezoidal pulse, a bi-phasic trapezoidal pulse, a mono-phasic sinusoidal pulse, a bi-phasic sinusoidal pulse, a mono-phasic pulse train series, a bi-phasic pulse train series, or a sinusoid.

14. The method of claim 8, wherein the waveform has a period of less than about 10 msec, wherein the waveform has a frequency between about 8 Hz and about 13 Hz, and/or wherein the strength of the magnetic field is less than about 500 milli-gauss.

15. The method of claim 8, wherein the method increases blood flow in the cortex of the subject.

16. The method of claim 8, wherein the method is effective to provide a treatment comprising improving cognitive function, improving executive function, improving academic performance, improving sports performance, improving neuropathic pain in the subject, improving a neurological disorder in the subject, improving a symptom of brain damage, or improving brain dysfunction in the subject, or improve at least one of an indication in the subject; a disorder in the subject; a symptom in the subject; a dysfunction in the subject; a characteristic in the subject; and any combination thereof.

17. The method of claim 16, wherein the indication is selected from the group consisting of replacement for meditation, quick nap, stress release, attention span, comprehension, memory, lowered blood pressure, increased libido, sports performance, academic performance, and any combination thereof;

wherein the disorder is selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof;

wherein the characteristic is selected from the group consisting of peripheral visual response, attention span, immediate reaction time (IRT), movement time (MT), simple perceptual reaction time (SPR), conflict perceptual reaction time (CPR), and any combination thereof;

wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia;

wherein the neurological disorder comprises at least one of a brain neurological disorder, a spinal cord disorder, a peripheral nervous system disorder, a cranial nerve disorder, an autonomic nervous system disorder, a seizure disorder, epilepsy, a movement disorder, a sleep disorder, a headache, lower back pain, neck pain, other generalized neuropathic pain, delirium, dementia, dizziness, vertigo, stupor, coma, a head injury, a stroke, multiple sclerosis, a demyelinating disease, an infection of the brain or spinal cord, a prion disease, and a complex regional pain syndrome;

wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage; and/or wherein the brain dysfunction comprises at least one of: aphasia, dysarthria, apraxia, agnosia, and amnesia.

18. The device of claim 8, wherein the first target frequency is the intrinsic alpha frequency (IAF) of the subject.

19. A method for treating a subject comprising:

generating a magnetic field using a Low Field Magnetic Stimulation device, wherein the Low Field Magnetic Stimulation device comprises a control that is configured to allow a user to adjust the magnetic field;

adjusting the magnetic field of the Low Field Magnetic Stimulation device by:

moving an intrinsic frequency of a subject up within an EEG band by using the control to generate a first frequency in the EEG band that is higher than the intrinsic frequency in the EEG band of the subject;

moving the intrinsic frequency of the subject down within the EEG band by using the control to generate a second frequency in the EEG band that is lower than the intrinsic frequency in the EEG band of the subject;

moving a Q-factor of the intrinsic frequency up by using the control to generate a first target frequency in the EEG band of the subject;

moving the Q-factor of the intrinsic frequency down by using the control to generate a second target frequency in the EEG band; or moving the Q-factor of the intrinsic frequency down by using a control to generate a plurality of frequencies, wherein each of the plurality of frequencies is within a pre-determined frequency range, and applying the magnetic field close to a head of the subject,
wherein the magnetic field has a strength of more than 0 Gauss and less than about 100 Gauss, and
wherein the Q-factor of the intrinsic frequency is the intrinsic frequency within the EEG band divided by a frequency bandwidth comprising frequencies that are within the EEG band and having energy at or above half of the energy at the intrinsic frequency within the EEG band.

20. The method of claim 19, wherein the magnetic field is generated by at least one of a Low Field Magnetic Stimulator (LFMS), a Magnetic Resonance Imager (MRI), a Transcranial Magnetic Stimulator (TMS), a Neuro-EEG Synchronization Therapy device, a picoTesla™ device, or any combination thereof.

* * * * *